United States Patent
Kharasch et al.

(10) Patent No.: US 9,091,690 B2
(45) Date of Patent: Jul. 28, 2015

(54) METHODS OF RENAL CANCER DETECTION

(75) Inventors: Evan David Kharasch, University City, MO (US); Jeremiah J. Morrissey, St. Louis, MO (US)

(73) Assignee: Washington University

( * ) Notice: Subject to any disclaimer, the term of this patent is extended or adjusted under 35 U.S.C. 154(b) by 122 days.

(21) Appl. No.: 13/321,331

(22) PCT Filed: May 18, 2010

(86) PCT No.: PCT/US2010/035270
§ 371 (c)(1),
(2), (4) Date: Jan. 10, 2012

(87) PCT Pub. No.: WO2010/135334
PCT Pub. Date: Nov. 25, 2010

(65) Prior Publication Data
US 2012/0115747 A1    May 10, 2012

Related U.S. Application Data

(60) Provisional application No. 61/179,012, filed on May 18, 2009.

(51) Int. Cl.
*G01N 33/566* (2006.01)
*G01N 33/574* (2006.01)

(52) U.S. Cl.
CPC .............................. *G01N 33/57438* (2013.01)

(58) Field of Classification Search
CPC ........................ G01N 33/57438; G01N 33/50
USPC ................ 436/501, 810, 813, 63, 64; 435/7.1
See application file for complete search history.

(56) References Cited

U.S. PATENT DOCUMENTS

2006/0252066 A1* 11/2006 Algate et al. ...................... 435/6

OTHER PUBLICATIONS

Gokden et al in "The Utility of PAX-2 in Distinguishing Metastatic Clear Cell Renal Cell Carcinoma From its Morphologic Mimics: An Immunohistochemical Study With Comparison to Renal Cell Carcinoma Marker" (Am J Surg Pathol Oct. 2008: vol. 32, pp. 1462-1467).*
Gnarra et al in "Expression of Pax-2 in Human Renal Cell Carcinoma and Growth Inhibition by Antisense Oligonucleotides" (Cancer Res 1995; vol. 55: pp. 4092-4098).*
Wasco et al in "Comparison of PAX-2, RCC Antigen, and Antiphosphorylated H2AX Antibody (y-H2AX) in Diagnosing Metastatic Renal Cell Carcinoma by Fine-Needle Aspiration" (Diagnostic Cytopathology, Aug. 2008: vol. 36, No. 8, pp. 568-573; published online Jul. 10, 2008).*
Skubitz et al in "Differential gene expression identifies subgroups of renal cell carcinoma" (J Lab Clin Med, 2006: vol. 147, No. 5, pp. 250-167).*
Bonventre, J.V., Kidney Injury Molecule-1 (KIM-1): a specific and sensitive biomarker of kidney injury. Scandinavian Journal of Clinical and Laboratory Investigation 241: 78-83, 2008.
Magni, F., et al., AQP1 expression analysis in human diseases: implications for proteomic characterization. Expert Rev. Proteomics 5: 29-43, 2008.
Lin, F., et al., Human kidney injury molecule-1 (hKIM-1): a useful immunohistochemical marker for diagnosing renal cell carcinoma and ovarian clear cell carcinoma. Am J Surg Pathol 31: 371-381, 2007.
Bosso, N., et al., Human urine biomarkers of renal cell carcinoma evaluated by ClinProt. Proteomics—Clinical Applications. Proteomics Clin Appl. 2: 1036-1046, 2008.
Ticozzi-Valerio, D., et al., Differential expression of AQP1 in microdomain-enriched membranes of Renal Cell Carcinoma. Proteomics Clin. Appl. 1: 588-597, 2007.
Mori, K, et al., Neutrophil gelatinase-associated lipocalin as the real-time indicator of active kidney damage. Kidney International 71: 967-970, 2007.
Signoretti, S., et al., Carbonic anhydrase IX as a predictive biomarker of response to kidney cancer therapy. BJU Int. 101 Suppl. 4:31-35, 2008.
Nogueira, M., et al., Molecular markers for predicting prognosis of renal cell carcinoma. Urologic Oncology 26: 113-124-847, 2008.
Seliger, B., et al., Identification of fatty acid binding proteins as markers associated with the initiation and/or progression of renal cell carcinoma. Proteomics 5: 2631-2640, 2005.
Perroud, B., et al., Pathway analysis of kidney cancer using proteomics and metabolic profiling. Molecular Cancer 5: 1-17, 2006.
Han, W.K., et al., Human kidney injury molecule-1 is a tissue and urinary tumor marker of renal cell carcinoma. J. Am. Soc. Nephrol. 16: 1126-1134, 2005.
Dorai, T., et al., Role of carbonic anhydrases in the progression of renal cell carcinoma subtypes: proposal of a unified hypothesis. Cancer Investigation 24:754-779, 2006.
Klatte, T., et al., Hypoxia-inducible factor 1 alpha in clear cell renal cell carcinoma. Clin. Cancer Res. 13: 7388-7393, 2007.
Bui, M.H.T., et al., Carbonic anhydrase IX is an independent predictor of survival in advanced renal clear cell carcinoma: implications for prognosis and therapy. Clin. Cancer Res. 9: 802-811, 2003.
Pantuck, A.J., et al., Carbonic anhydrase IX as a predictive biomarker for clear cell renal cell carcinoma. J. Clinical Oncology 26: 3105-3107, 2008.

(Continued)

*Primary Examiner* — Catherine S Hibbert
(74) *Attorney, Agent, or Firm* — Saul L. Zackson; Zackson Law LLC

(57) ABSTRACT

Disclosed are methods for detecting, diagnosing or monitoring a renal cancer in a subject. The methods include detecting quantity of one or more polypeptides or fragments thereof comprised by body fluid such as urine, wherein the one or more polypeptides or fragments thereof, can be present at elevated levels in a subject with a kidney cancer, as compared to a subject without a kidney cancer. Non-limiting examples of such polypeptides include aquaporin-1, adipose differentiation-related protein and paired box protein-2. Antibody probes can be used to detect or quantify the polypeptides. In some embodiments, mass spectroscopy can be used to detect or quantify the polypeptides, or to identify a polypeptide in a body fluid sample from a subject with a kidney cancer.

6 Claims, 12 Drawing Sheets

(56) References Cited

OTHER PUBLICATIONS

Devarajan, P., Neutrophil gelatinase-associated lipocalin (NGAL): a new marker of kidney disease. Scandinavian Journal of Clinical & Laboratory Investigation 68(S241): 89-94, 2008.
Vaidya, V.S., et al., Biomarkers of acute kidney injury. Annu. Rev. Pharmacol. Toxicol 48: 463-493, 2008.
Hu, J., et al., Increased migration and metastatic potential of tumor cells expressing aquaporin water channels. FASEB J. 20: 1892-1894, 2006.
Huang, Y., et al., Expression of aquaporin 1 in primary renal tumors: a prognostic indicator for clear-cell renal cell carcinoma. Eur Urol. 56: 690-698, 2009.
Mazal, P.R., et al., Expression of aquaporins and PAX-2 compared to CD10 and cytokeratin 7 in renal neoplasms: a tissue microarray study. Mod. Pathol. 18: 535-540, 2005.
Takenawa, J., et al., Transcript levels of aquaporin 1 and carbonic anhydrase IV as predictive indicators for prognosis of renal cell carcinoma patients after nephrectomy. Int. J. Cancer 79: 1-7, 1998.
Yao, M. et al., Gene expression analysis of renal carcinoma: adipose differentiation-related protein as a potential diagnostic and prognostic biomarker for clear-cell renal carcinoma Clin. Cancer Res. 13: 152-160, 2007.
Yao, M. et al., Expression of adipose differentiation-related protein: a predictor of cancer-specific survival in clear cell renal carcinoma. J. Pathol. 205: 377-387, 2005.
Kim, K., et al., Urine Metabolomics Analysis for Kidney Cancer Detection and Biomarker Discovery. Mol. Cell Proteomics, 8: 558-570, 2009.
Seliger, B., et al., Candidate biomarkers in renal cell carcinoma. Proteomics 7: 4601-4612, 2007.
Pisitkun, T., et al., Identification and proteomic profiling of exosomes in human urine. Proc Natl Acad Sci USA 101: 13368-13373, 2004.
Zhou, H., et al., Urinary exosomal transcription factors, a new class of biomarkers for renal disease. Kidney Int. 74: 613-621, 2008.
Gokden, N., et al., The utility of Pax-2 as an immunohistochemical marker for renal cell carcinoma in cytopathology. Diagnostic Cytopathology 36: 473-477, 2008.
Cheruvanky, A., et al., Rapid isolation of urinary exosomal biomarkers using a nanomembrane ultrafiltration concentrator. Am. J. Physiol. 292: F1657-F1661, 2007.
Zhou, H. et al., Collection, storage, preservation, and normalization of human urinary exosomes for biomarker discovery. Kidney Int'l 69: 1471-1476, 2006.
Takata, K., et al., Localization and trafficking of aquaporin 2 in the kidney. Histochem Cell Biol 130: 197-209, 2008.
Pisitkun, T, et al., Discovery of urinary biomarkers. Molecular & Cellular Proteomics 5: 1760-1771, 2006.
Supplementary European Search Report, pursuant to Rule 62 EPC, mail date Jan. 2, 2013.
Goligorsky et al. "Diagnostic Potential of Urine Proteome: A Broken Mirror of Renal Diseases" J. Am. Soc. of Neph. 18:2233-9, 2007.
Mazal et al. "Expression of aquaporins and PAX-2 compared to CD10 and cytokeratin 7 in renal neoplasms: a tissue microarray study" Modern Pathology, 18:538-9, 2004.
Pisitkun et al. "Discovery of urinary biomarkers" Molecular & Cellular Proteomics, pp. 1760-1771, 2006.
Zhou et al. "Collection, storage, preservation, and normalization of human urinary exosomes for biomarker discovery" Kidney Intl., 69:1471-6, 2006.
Rogers et al. "Proteomic profiling of urinary proteins in renal cancer by surface enhanced laser desorption inonization and neural-network analysis; Identification of key issues affecting potential clinical utility" Cancer Research, Am. Ass. for Cancer Research, 63:6971-83, 2003.
Morrissey et al. "Urinary biomarkers for the early diagnosis of kidney cancer" Mayo Clinic Proceedings, 85:413-21, 2010.
Higgins, J.P.T. et al: "Gene expression patterns in renal cell carcinoma assessed by complementary DNA microarray", American Journal of Pathology; [10640]. Elsevier Inc. US. vol. 162. No. 3. Mar. 1, 2003 pp. 925-932.
Kramer et al. "Can Aquaporin-1 and Adipophilin in Urine Distinguish Between Malignant and Nonmalignant Renal Lesions?" vol. 85. No. 8. Aug. 1, 2010 p. 768.
Morrissey Jeremiah J et al: "Urinary Biomarkers for the Early Diagnosis of Kidney Cancer" Mayo Clinic Proceedings. Dowden Health Media. Inc. US. vol 85. No. 5. May 1, 2010. pp. 413-421.

\* cited by examiner

FIG. 5 Renal Dipeptidase 1

SEQUENCE LISTING

<160> NUMBER OF SEQ ID NOS: 7

<210> SEQ ID NO 1
<211> LENGTH: 269
<212> TYPE: PRT
<213> ORGANISM: Homo sapiens

<400> SEQUENCE: 1

Met Ala Ser Glu Phe Lys Lys Lys Leu Phe Trp Arg Ala Val Val Ala
1               5                   10                  15

Glu Phe Leu Ala Thr Thr Leu Phe Val Phe Ile Ser Ile Gly Ser Ala
            20                  25                  30

Leu Gly Phe Lys Tyr Pro Val Gly Asn Asn Gln Thr Ala Val Gln Asp
        35                  40                  45

Asn Val Lys Val Ser Leu Ala Phe Gly Leu Ser Ile Ala Thr Leu Ala
    50                  55                  60

Gln Ser Val Gly His Ile Ser Gly Ala His Leu Asn Pro Ala Val Thr
65                  70                  75                  80

Leu Gly Leu Leu Leu Ser Cys Gln Ile Ser Ile Phe Arg Ala Leu Met
                85                  90                  95

Tyr Ile Ile Ala Gln Cys Val Gly Ala Ile Val Ala Thr Ala Ile Leu
            100                 105                 110

Ser Gly Ile Thr Ser Ser Leu Thr Gly Asn Ser Leu Gly Arg Asn Asp
        115                 120                 125

Leu Ala Asp Gly Val Asn Ser Gly Gln Gly Leu Gly Ile Glu Ile Ile
    130                 135                 140

Gly Thr Leu Gln Leu Val Leu Cys Val Leu Ala Thr Thr Asp Arg Arg
145                 150                 155                 160

```
Arg Arg Asp Leu Gly Gly Ser Ala Pro Leu Ala Ile Gly Leu Ser Val
            165                 170                 175

Ala Leu Gly His Leu Leu Ala Ile Asp Tyr Thr Gly Cys Gly Ile Asn
        180                 185                 190

Pro Ala Arg Ser Phe Gly Ser Ala Val Ile Thr His Asn Phe Ser Asn
        195                 200                 205

His Trp Ile Phe Trp Val Gly Pro Phe Ile Gly Ala Leu Ala Val
        210                 215                 220

Leu Ile Tyr Asp Phe Ile Leu Ala Pro Arg Ser Ser Asp Leu Thr Asp
225                 230                 235                 240

Arg Val Lys Val Trp Thr Ser Gly Gln Val Glu Glu Tyr Asp Leu Asp
                245                 250                 255

Ala Asp Asp Ile Asn Ser Arg Val Glu Met Lys Pro Lys
            260                 265
```

<210> SEQ ID NO 2
<211> LENGTH: 437
<212> TYPE: PRT
<213> ORGANISM: Homo sapiens

<400> SEQUENCE: 2

```
Met Ala Ser Val Ala Val Asp Pro Gln Pro Ser Val Val Thr Arg Val
1               5                   10                  15

Val Asn Leu Pro Leu Val Ser Ser Thr Tyr Asp Leu Met Ser Ser Ala
                20                  25                  30

Tyr Leu Ser Thr Lys Asp Gln Tyr Pro Tyr Leu Lys Ser Val Cys Glu
            35                  40                  45

Met Ala Glu Asn Gly Val Lys Thr Ile Thr Ser Val Ala Met Thr Ser
        50                  55                  60

Ala Leu Pro Ile Ile Gln Lys Leu Glu Pro Gln Ile Ala Val Ala Asn
65                  70                  75                  80

Thr Tyr Ala Cys Lys Gly Leu Asp Arg Ile Glu Glu Arg Leu Pro Ile
                85                  90                  95

Leu Asn Gln Pro Ser Thr Gln Ile Val Ala Asn Ala Lys Gly Ala Val
                100                 105                 110

Thr Gly Ala Lys Asp Ala Val Thr Thr Thr Val Thr Gly Ala Lys Asp
            115                 120                 125

Ser Val Ala Ser Thr Ile Thr Gly Val Met Asp Lys Thr Lys Gly Ala
        130                 135                 140

Val Thr Gly Ser Val Glu Lys Thr Lys Ser Val Ser Gly Ser Ile
145                 150                 155                 160

Asn Thr Val Leu Gly Ser Arg Met Met Gln Leu Val Ser Ser Gly Val
                165                 170                 175

Glu Asn Ala Leu Thr Lys Ser Glu Leu Leu Val Glu Gln Tyr Leu Pro
                180                 185                 190

Leu Thr Glu Glu Glu Leu Glu Lys Glu Ala Lys Lys Val Glu Gly Phe
            195                 200                 205

Asp Leu Val Gln Lys Pro Ser Tyr Tyr Val Arg Leu Gly Ser Leu Ser
        210                 215                 220

Thr Lys Leu His Ser Arg Ala Tyr Gln Gln Ala Leu Ser Arg Val Lys
225                 230                 235                 240

Glu Ala Lys Gln Lys Ser Gln Gln Thr Ile Ser Gln Leu His Ser Thr
                245                 250                 255

Val His Leu Ile Glu Phe Ala Arg Lys Asn Val Tyr Ser Ala Asn Gln
```

```
                         260                 265                 270
Lys Ile Gln Asp Ala Gln Asp Lys Leu Tyr Leu Ser Trp Val Glu Trp
                275                 280                 285

Lys Arg Ser Ile Gly Tyr Asp Thr Asp Glu Ser His Cys Ala Glu
        290                 295                 300

His Ile Glu Ser Arg Thr Leu Ala Ile Ala Arg Asn Leu Thr Gln Gln
305                 310                 315                 320

Leu Gln Thr Thr Cys His Thr Leu Leu Ser Asn Ile Gln Gly Val Pro
                325                 330                 335

Gln Asn Ile Gln Asp Gln Ala Lys His Met Gly Val Met Ala Gly Asp
                340                 345                 350

Ile Tyr Ser Val Phe Arg Asn Ala Ala Ser Phe Lys Glu Val Ser Asp
                355                 360                 365

Ser Leu Leu Thr Ser Ser Lys Gly Gln Leu Gln Lys Met Lys Glu Ser
        370                 375                 380

Leu Asp Asp Val Met Asp Tyr Leu Val Asn Asn Thr Pro Leu Asn Trp
385                 390                 395                 400

Leu Val Gly Pro Phe Tyr Pro Gln Leu Thr Glu Ser Gln Asn Ala Gln
                405                 410                 415

Asp Gln Gly Ala Glu Met Asp Lys Ser Ser Gln Glu Thr Gln Arg Ser
                420                 425                 430

Glu His Lys Thr His
        435

<210> SEQ ID NO 3
<211> LENGTH: 416
<212> TYPE: PRT
<213> ORGANISM: Homo sapiens

<400> SEQUENCE: 3

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
                20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
                180                 185                 190
```

```
Ile Pro Arg Ser Asn Gly Glu Lys Arg Lys Arg Asp Glu Val Glu Val
            195                 200                 205

Tyr Thr Asp Pro Ala His Ile Arg Gly Gly Gly Leu His Leu Val
210                 215                 220

Trp Thr Leu Arg Asp Val Ser Glu Gly Ser Val Pro Asn Gly Asp Ser
225                 230                 235                 240

Gln Ser Gly Val Asp Ser Leu Arg Lys His Leu Arg Ala Asp Thr Phe
                245                 250                 255

Thr Gln Gln Gln Leu Glu Ala Leu Asp Arg Val Phe Glu Arg Pro Ser
            260                 265                 270

Tyr Pro Asp Val Phe Gln Ala Ser Glu His Ile Lys Ser Glu Gln Gly
        275                 280                 285

Asn Glu Tyr Ser Leu Pro Ala Leu Thr Pro Gly Leu Asp Glu Val Lys
    290                 295                 300

Ser Ser Leu Ser Ala Ser Thr Asn Pro Glu Leu Gly Ser Asn Val Ser
305                 310                 315                 320

Gly Thr Gln Thr Tyr Pro Val Val Thr Gly Arg Asp Met Ala Ser Thr
                325                 330                 335

Thr Leu Pro Gly Tyr Pro Pro His Val Pro Pro Thr Gly Gln Gly Ser
            340                 345                 350

Tyr Pro Thr Ser Thr Leu Ala Gly Met Val Pro Gly Ser Glu Phe Ser
        355                 360                 365

Gly Asn Pro Tyr Ser His Pro Gln Tyr Thr Ala Tyr Asn Glu Ala Trp
    370                 375                 380

Arg Phe Ser Asn Pro Ala Leu Leu Ser Ser Pro Tyr Tyr Tyr Ser Ala
385                 390                 395                 400

Ala Pro Arg Ser Ala Pro Ala Ala Ala Ala Ala Tyr Asp Arg His
                405                 410                 415

<210> SEQ ID NO 4
<211> LENGTH: 393
<212> TYPE: PRT
<213> ORGANISM: Homo sapiens

<400> SEQUENCE: 4

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
                20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160
```

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
    210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
    290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
        355                 360                 365

Leu Ser Ser Pro Tyr Tyr Tyr Ser Ala Ala Pro Arg Ser Ala Pro Ala
    370                 375                 380

Ala Ala Ala Ala Ala Tyr Asp Arg His
385                 390

<210> SEQ ID NO 5
<211> LENGTH: 396
<212> TYPE: PRT
<213> ORGANISM: Homo sapiens

<400> SEQUENCE: 5

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln

```
                130                 135                 140
Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
                180                 185                 190

Ile Pro Arg Ser Asn Gly Glu Lys Arg Lys Arg Asp Glu Asp Val Ser
                195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
                260                 265                 270

Leu Thr Pro Gly Leu Asp Glu Val Lys Ser Ser Leu Ser Ala Ser Thr
                275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Glu Ala Ala Val Gly Pro Ser Ser Ser Leu Met Ser
                340                 345                 350

Lys Pro Gly Arg Lys Leu Ala Glu Val Pro Pro Cys Val Gln Pro Thr
                355                 360                 365

Gly Ala Ser Ser Pro Ala Thr Arg Thr Ala Thr Pro Ser Thr Arg Pro
                370                 375                 380

Thr Thr Arg Leu Gly Asp Ser Ala Thr Pro Pro Tyr
385                 390                 395

<210> SEQ ID NO 6
<211> LENGTH: 408
<212> TYPE: PRT
<213> ORGANISM: Homo sapiens

<400> SEQUENCE: 6

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
                20                  25                  30

Leu Pro Asp Val Val Arg Gln Arg Ile Val Glu Leu Ala His Gln Gly
                35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
                100                 105                 110
```

-continued

Glu Ile Arg Asp Arg Leu Leu Ala Glu Gly Ile Cys Asp Asn Asp Thr
            115                 120                 125

Val Pro Ser Val Ser Ser Ile Asn Arg Ile Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
        355                 360                 365

Leu Met Pro Pro Gly Pro Pro Leu Pro Leu Leu Pro Leu Pro Met
370                 375                 380

Thr Ala Thr Ser Tyr Arg Gly Asp His Ile Lys Leu Gln Ala Asp Ser
385                 390                 395                 400

Phe Gly Leu His Ile Val Pro Val
                405

<210> SEQ ID NO 7
<211> LENGTH: 431
<212> TYPE: PRT
<213> ORGANISM: Homo sapiens

<400> SEQUENCE: 7

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

```
Gly Val Ile Gly Gly Ser Lys Pro Lys Val Ala Thr Pro Lys Val Val
                    85                  90                  95
Asp Lys Ile Ala Glu Tyr Lys Arg Gln Asn Pro Thr Met Phe Ala Trp
                100                 105                 110
Glu Ile Arg Asp Arg Leu Leu Ala Glu Gly Ile Cys Asp Asn Asp Thr
                115                 120                 125
Val Pro Ser Val Ser Ser Ile Asn Arg Ile Ile Arg Thr Lys Val Gln
            130                 135                 140
Gln Pro Phe His Pro Thr Pro Asp Gly Ala Gly Thr Gly Val Thr Ala
145                 150                 155                 160
Pro Gly His Thr Ile Val Pro Ser Thr Ala Ser Pro Val Ser Ser
                165                 170                 175
Ala Ser Asn Asp Pro Val Gly Ser Tyr Ser Ile Asn Gly Ile Leu Gly
                180                 185                 190
Ile Pro Arg Ser Asn Gly Glu Lys Arg Lys Arg Asp Glu Val Glu Val
            195                 200                 205
Tyr Thr Asp Pro Ala His Ile Arg Gly Gly Gly Leu His Leu Val
    210                 215                 220
Trp Thr Leu Arg Asp Val Ser Glu Gly Ser Val Pro Asn Gly Asp Ser
225                 230                 235                 240
Gln Ser Gly Val Asp Ser Leu Arg Lys His Leu Arg Ala Asp Thr Phe
                245                 250                 255
Thr Gln Gln Gln Leu Glu Ala Leu Asp Arg Val Phe Glu Arg Pro Ser
                260                 265                 270
Tyr Pro Asp Val Phe Gln Ala Ser Glu His Ile Lys Ser Glu Gln Gly
            275                 280                 285
Asn Glu Tyr Ser Leu Pro Ala Leu Thr Pro Gly Leu Asp Glu Val Lys
    290                 295                 300
Ser Ser Leu Ser Ala Ser Thr Asn Pro Glu Leu Gly Ser Asn Val Ser
305                 310                 315                 320
Gly Thr Gln Thr Tyr Pro Val Val Thr Gly Arg Asp Met Ala Ser Thr
                325                 330                 335
Thr Leu Pro Gly Tyr Pro Pro His Val Pro Pro Thr Gly Gln Gly Ser
                340                 345                 350
Tyr Pro Thr Ser Thr Leu Ala Gly Met Val Pro Gly Ser Glu Phe Ser
            355                 360                 365
Gly Asn Pro Tyr Ser His Pro Gln Tyr Thr Ala Tyr Asn Glu Ala Trp
    370                 375                 380
Arg Phe Ser Asn Pro Ala Leu Leu Met Pro Pro Pro Gly Pro Pro Leu
385                 390                 395                 400
Pro Leu Leu Pro Leu Pro Met Thr Ala Thr Ser Tyr Arg Gly Asp His
                405                 410                 415
Ile Lys Leu Gln Ala Asp Ser Phe Gly Leu His Ile Val Pro Val
                420                 425                 430
```

US 9,091,690 B2

METHODS OF RENAL CANCER DETECTION

PRIORITY STATEMENT

This application is a national application of PCT application PCT/US10/35270 filed May 10, 2010, which claims priority from U.S. Provisional Application No. 61/179,012, filed on May 18, 2009. Each of these applications is incorporated herein by reference in its entirety.

INCORPORATION-BY-REFERENCE OF MATERIAL SUBMITTED IN COMPUTER READABLE FORM

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

INTRODUCTION

Renal cancer accounts for about 3% of the cancers but is usually diagnosed indirectly when individuals are evaluated by imaging techniques such as CT, ultrasound or MRI for unrelated causes (Nogueira, M., et al., Urologic Oncology 26: 113-124-847, 2008; Jemal, A., et al., CA Cancer J. Clin. 57: 43-66, 2007; Levy, D. A., et al., J. Urol. 159: 1163-1167, 1998; Pantuck, A. J., et al., J. Urol. 166: 1611-1623, 2001; Figlin, R. A., J. Urol. 161: 381-386; Discussion 6-7, 1999; Cohen, H. T., et al., New Engl. J. Med. 353: 2477-2490, 2005). Renal clear cell and papillary cancers, which arise from the proximal tubule, together account for approximately 90% of all renal cancers (Linehan, J. A., et al., Curr. Opin. Urol. 19: 133-137, 2009; Cohen, H. T., et al., N. Engl. J. Med. 353: 2477-2490, 2005; Jemal, A., et al., CA Cancer J. Clin. 58: 71-96, 2008. Frequently, by the time renal cancer is directly diagnosed due to its symptoms, the tumor has advanced beyond a curative stage, and has metastasized to nearby lymph nodes or other organs in 30-40% of affected individuals (Jemal, A., et al., CA Cancer J Clin 57: 43-66, 2007; Levy, D. A., et al., J. Urol. 159: 1163-1167, 1998). The prognosis for those patients where the cancer has metastasized is poor since these cancers have some resistance to chemotherapy; the 5 year survival is 5% or less (Pantuck, A. J., et al., J. Urol. 166: 1611-1623, 2001; Figlin, R. A., J. Urol. 161: 381-386; Discussion 6-7, 1999; Cohen, H. T., et al., New Engl. J. Med. 353: 2477-2490, 2005). If at the time of diagnosis, the tumor is confined within the kidney capsule, survival is usually quite good and can exceed 70%, however, up to 30% of patients with no discernable metastasis at the time of nephrectomy will go on to have metastatic disease (Pantuck, A. J., et al., J. Urol. 166: 1611-1623, 2001; Figlin, R. A., J. Urol. 161: 381-386; Discussion 6-7, 1999; Cohen, H. T., et al., New Engl. J. Med. 353: 2477-2490, 2005). In the year 2007 there were 51,190 new cases of kidney cancer diagnosed and 12,840 deaths were due to this disease in the United States. The economic impact of the disease is devastating. In the year 2000, over $400 million was spent in the United States alone on care for kidney cancer with the vast majority of the expenditures for inpatient care (Wallen, E., et al., J. Urol. 177: 2006-2019, 2007). Risk factors associated with kidney cancer include, but are not limited to, smoking (Haddock, C. K., Military Medicine, Nov. 2000; Basu, S., US Medicine, May 2004; Parker, A., et al., Int'l. J. Urology 15:304-308, 2008; Stewart, J., et al., J. Am. Soc. Nephrol. 14:197-207, 2003) and exposure to solvents such as trichloroethylene used to degrease equipment (National Research Council, National Academy of Sciences: Assessing the Human Health Risks of Trichloroethylene. 58-136, 2006). In addition to smoking; obesity, hypertension and acquired cystic kidney disease due to end stage kidney disease are other important risk factors (Stewart, J., et al., J. Am. Soc. Nephrol. 14:197-207, 2003). Toxic nephropathies resulting in dialysis increase the risk of renal parenchymal cancers and this risk steadily increases with increasing length of dialysis (Stewart, J., et al., J. Am. Soc. Nephrol. 14:197-207, 2003). Previous studies by many groups have characterized gene and protein expression in surgically removed tumor tissue (Seliger, B., et al., Proteomics 5: 2631-2640, 2005; Perroud, B., et al., Molecular Cancer 5: 1-17, 2006; Banks, R. E., et al., World J. Urol. 25: 537-556, 2007; Ramankulov, A., et al., Cancer Sci. 99: 1188-1194, 2008; Domoto, T., et al., Cancer Sci. 98: 77-82, 2007; Han, W. K., et al., J. Am. Soc. Nephrol. 16: 1126-1134, 2005; Teratani, T., et al., J. Urol. 69: 236-240, 2007; Dorai, T., et al., Cancer Investigation 24:754-779, 2006; Klatte, T., et al., Clin. Cancer Res. 13: 7388-7393, 2007; Bui, M. H. T., et al., Clin. Cancer Res. 9: 802-811, 2003; Signoretti, S., et al., BJU Int. 101 Suppl. 4:31-35, 2008; Pantuck, A. J., et al., J. Clinical Oncology 26: 3105-3107, 2008) but these techniques have not translated into any clinically relevant assays in use now to diagnose kidney cancer prospectively.

Many of the proposed markers studied to date, while expressed in high frequency in kidney cancers, are also expressed in other cancers (Domoto, T., et al., Cancer Sci. 98: 77-82, 2007) or kidney diseases (Ramankulov, A., et al., Cancer Sci. 99: 1188-1194, 2008).

Some biomarkers have been identified which can serve as general kidney injury biomarkers but are not specific for renal cell cancers. Neutrophil gelatinase-associated lipocalin (NGAL), a member of the lipocalin superfamily, is produced in the kidney during organogenesis and participates in mesenchymal to epithelial differentiation during kidney development (Mori, K., et al., Kidney International 71: 967-970, 2007). NGAL expression within the mature kidney is low but detectable, however, within an hour of kidney injury (regardless of etiology) NGAL expression increases in log-orders such that urinary NGAL measurements need not be corrected by creatinine excretion (Mori, K., et al., Kidney International 71: 967-970; 2007; Devarajan, P., Scandinavian Journal of Clinical & Laboratory Investigation 68(S241): 89-94, 2008). Since NGAL induction is detectable within an hour, it may be considered an immediate early gene or an acute phase reactant (Mori, K., et al., Kidney International 71: 967-970; 2007; Devarajan, P., Scandinavian Journal of Clinical & Laboratory Investigation 68(S241): 89-94, 2008). Changes in urinary NGAL levels were used as a biomarker of acute kidney injury since it significantly correlated with future changes in the serum creatinine concentration (Mori, K., et al., Kidney International 71: 967-970; 2007). Application of NGAL as a biomarker for renal cell carcinoma has not been reported. However, an early report suggests that NGAL does not appear to be induced in this form of renal cell dedifferentiation (Friedl, A., et al., The Histochemical Journal 31: 433-441, 1999). Like NGAL, kidney injury molecule-1 (KIM-1) was initially discovered by measuring differential gene expression and was one of a few genes up-regulated 10-fold or more following acute kidney injury in animal models of disease; A proteolytic exodomain fragment of KIM-1 is excreted in the in the urine of the injured kidney regardless of the etiology of the injury (Bonventre, J. V., Scandinavian Journal of Clinical and Laboratory Investigation 241: 78-83, 2008; Vaidya, V. S., et al., Annu. Rev. Pharmacol. Toxicol 48: 463-493, 2008; Ferguson, M. A., et al., Toxicology 245: 182-193, 2008). Measured as HAVCR-1, KIM-1 expression was found to be increased in 8 of 13 clear cell carcinomas but not by any of 5 oncocytomas (Vila, M. R., et al., Kidney international 65: 1761-1773; 2004). Urinary KIM-1 levels were significantly increased in patients with clear cell and papillary tumors but were significantly decreased following the surgical removal of the affected kidney (Han, W. K., et al., J. Am. Soc. Nephrol. 16: 1126-1134, 2005). A follow-up immunohistochemical study supported the concept that KIM-1 is a sensitive and specific marker of papillary and clear cell carcinomas and sporadic oncocytomas (Lin, F., et al., Am J Surg Pathol 31: 371-381, 2007). Nevertheless, KIM-1 is also overexpressed and excreted in the urine from patients with numerous types of kidney injury, such as that due to diabetes mellitus, glomerulosclerosis, IgA nephropathy, nephrotoxicants, and ischemic injury (Bonventre, J. V., et al., Scand J. Clin. Lab Invest. Suppl. 241: 78-83, 2008; Ferguson, M. A., et al., Toxicology 245: 182-193, 2008; Vaidya, V. S., et al., Annu. Rev. Pharmacol. Toxicol. 48: 463-493, 2008). Thus, KIM-1 is a nonspecific biomarker of any kidney injury and lacks the specificity needed for a biomarker of kidney cancer.

Aquaporin-1 (AQP-1) is a water channel protein present in the apical membrane of the proximal tubule but can increase the migration and metastatic potential of tumor cells (Hu, J., et al., FASEB J. 20: 1892-1894, 2006). AQP-1 was found by expression array analysis of excised renal tumors to have increased expression (Huang, Y., et al., Eur Urol. 56: 690-698, 2009; Magni, F., et al., Expert Rev. Proteomics 5: 29-43, 2008; Mazal, P. R., et al., Mod. Pathol. 18: 535-540, 2005; Takenawa, J., et al., Int. J. Cancer 79: 1-7, 1998).

Adipophilin is a protein associated with lipid droplets (Bickel, P. E., et al., Biochim. Biophys. Acta 1791: 419-440, 2009), a prominent pathologic feature of clear cell carcinoma (Tickoo, S. K., et al., Urol. Clin. North Am. 35: 551-561, 2008) and those of macrophages. (Llorente-Cortes, V. et al., J. Lipid Res. 48: 2133-2140, 2007; Urahama, Y., et al., Am. J. Pathol. 173: 1286-1294, 2008). Lipid droplets, in addition to accumulated glycogen granules, account for the histologic clearness of the cells. Moreover, papillary carcinomas are associated with abundant lipid-laden macrophages (Tickoo, S. K., et al., Urol. Clin. North Am. 35: 551-561, 2008). Expression of ADFP was found to be up-regulated in surgically excised renal tumor tissue (Yao, M. et al., Clin. Cancer Res. 13: 152-160, 2007; Yao, M. et al., J. Pathol. 205: 377-387, 2005; Yao, M. et al, Int. J. Cancer 123: 1126-1132, 2008; Zhao, H. et al., PLoS Med. 3: e13, 2006). ADFP has target epitopes for possible antigen-specific cytotoxic T-lymphocyte-mediated immunotherapy (Schmidt, S. M. et al., Cancer Res. 64: 1164-1170, 2004; Wierecky, J. et al., Cancer Res. 66: 5910-5918, 2006).

There are many expression or tissue microarray studies that characterize potential biomarkers of renal cancer (George, S., et al., Expert Rev. Anticancer Ther. 7: 1737-1747, 2007; Huang, Y., et al., Eur. Urol. 56: 690-698, 2009; Kim, K., et al., Mol. Cell Proteomics, 8: 558-570, 2009; Magni, F., Expert Rev. Proteomics 5: 29-43, 2008; Mazal, P. R., et al., Mod. Pathol. 18: 535-540, 2005; Parker, A. S., et al., Cancer 115: 2092-2103, 2009; Ramankulov, A., et al., Cancer Sci. 99: 1188-1194, 2008; Ramankulov, A., et al., Cancer Lett. 269: 85-92, 2008; Takenawa J., et al., Int. J. Cancer 79: 1-7, 1998; Teratani, T., et al. Urology 69: 236-240, 2007); however, these studies have not yielded any candidate markers for testing in urine. Only a few studies have examined urine as a potential source of biomarkers for renal cancer, and these focused on fragments of uromodulin and serum amyloid A (Parker, A. S., et al., Cancer 115: 2092-2103, 2009; Ramankulov, A., et al., Cancer Lett. 269: 85-92, 2008; Seliger, B., et al., Proteomics 7: 4601-4612, 2007) or undefined proteins uncovered by mass spectrometry (Seliger, B., et al., Proteomics 7: 4601-4612, 2007). Many of the proposed markers studied to date, although expressed in high frequency in patients with kidney cancers, are also expressed in patients with other cancers (Lin, F., Am. J. Surg. Pathol. 31: 371-381, 2007; Ramankulov, A., et al., Cancer Sci. 99: 1188-1194, 2008; Teratani, T., et al. Urology 69: 236-240, 2007) or kidney diseases (Han, W. K., et al., J. Am. Soc. Nephrol. 16: 1126-1134, 2005; Bonventre, J. V., et al., Scand J. Clin. Lab Invest. Suppl. 241: 78-83, 2008; Ferguson, M. A., et al., Toxicology 245: 182-193, 2008; Vaidya, V. S., et al., Annu. Rev. Pharmacol. Toxicol. 48: 463-493, 2008). This mutes their specificity, which is required of a kidney cancer biomarker. In addition to urine proteins, the urinary metabolomic profile has been considered as a source of potential biomarkers of kidney cancer (Perroud, B., et al., Mol. Cancer 5: 64, 2006). However, a recent study found that the qualitative and quantitative pattern of urinary metabolites was influenced by patient diet, time of day of sample collection, and area of the country of the participating sites and that it could not reliably distinguish urinary metabolites of the same patient before tumor excision compared with after tumor excision (Kim, K., et al., Mol. Cell Proteomics, 8: 558-570, 2009). This casts doubt on the current reliability of metabolomics as a diagnostic approach to screen even at-risk populations for kidney cancer.

Urinary exosomes are vesicular structures released by fusion of multivesicular bodies to the apical membrane (Pisitkun T., et al., Proc Natl Acad Sci USA 101: 13368-13373, 2004; Fevrier, B., et al., Current Opinion in Cell Biology 16: 415-421, 2004; Gonzales, P., et al., Nephrol Dial Transplant. 23: 1799-1801, 2008) and, at least in the urine, represent material from cells of all parts of the nephron including the glomerulus (Pisitkun T., et al., Proc Natl Acad Sci USA 101: 13368-13373, 2004). These 30-100 nm intraluminal vesicles are released constitutively and in regulated fashion (Fevrier, B., et al., Current Opinion in Cell Biology 16: 415-421, 2004; Gonzales, P., et al., Nephrol Dial Transplant. 23: 1799-1801, 2008). The exosomes are, in essence, a right-side-out biopsy of the cells of origin (Gonzales, P., et al., Nephrol Dial Transplant. 23: 1799-1801, 2008). Exosomes also contain a sampling of cytosolic proteins of the parent cell such that transcription factors with a finite cytosolic presence are trapped within (Zhou. H., et al., Kidney Int. 74: 613-621, 2008).

Several studies have compared gene or protein expression between the kidney tumors and adjacent normal kidney from nephrectomy material (Seliger, B., et al., Proteomics 5: 2631-2640, 2005; Perroud, B., et al., Molecular Cancer 5: 1-17, 2006; Banks, R. E., et al., World J Urol 25: 537-556, 2007; Ramankulov, A., et al., Cancer Sci. 99: 1188-1194, 2008; Domoto, T., et al., Cancer Sci. 98: 77-82, 2007; Han, W. K., et al., J Am Soc Nephrol. 16: 1126-1134, 2005; Teratani, T., et al., J Urol. 69: 236-240, 2007; Dorai, T., et al., Cancer Investigation 24:754-779, 2006; Klatte, T., et al., Clin. Cancer Res. 13: 7388-7393, 2007; Bui, M. H. T., et al., Clin. Cancer Res. 9: 802-811, 2003; Signoretti, S., et al., BJU Int. 101 Suppl 4:31-35, 2008; Pantuck, A. J., et al., J. Clinical Oncology 26: 3105-3107, 2008). These are assays on tumor tissue. One study on urine markers found uromodulin (Tamm Horsfall protein) and serum amyloid alpha-1 (Bosco, N., et al., Proteomics Clin Appl. 2: 1036-1046, 2008) but their specificity to renal cancer can be questioned. Proximal tubule epithelial cells dedifferentiate in a wide variety of kidney diseases and this is true of renal cell carcinoma. Gene expression analysis of differentiation markers found that aquaporin-1 (AQP1) was expressed in early but not late stages of renal carcinoma (Takenawa, J., et al., Int. J. Cancer (Pred. Oncol.) 79: 1-7, 1998; Mazal. P. R., et al., Modern Pathology 18: 535-540, 2005; Ticozzi-Valerio, D., et al., Proteomics Clin. Appl. 1: 588-597, 2007; Magni, F., et al., Expert Rev. Proteomics 5: 29-43, 2008.; Gokden, N., et al., Diagnostic Cytopathology 36: 473-477, 2008; Austruy, E., et al., Cancer Research 53: 2888-2894, 1993). The disappearance of aquaporin-1 gene expression was found by multivariate analysis to predict poor outcomes (Takenawa, J., et al., Int. J. Cancer (Pred. Oncol.) 79: 1-7, 1998; Mazal. P. R., et al., Modern Pathology 18: 535-540, 2005). This was subsequently born out in immuno-histochemical studies for aquaporin-1 and, in addition, for the expression of PAX-2, a nuclear transcription factor expressed during kidney development (Mazal. P. R., et al., Modern Pathology 18: 535-540, 2005; Gokden, N., et al., Diagnostic Cytopathology 36: 473-477, 2008). Another marker, CD 10, was elevated in renal cell carcinoma and its expression remained elevated independent of nuclear grade while that of aquaporin-1 and PAX-2 declined (Mazal. P. R., et al., Modern Pathology 18: 535-540, 2005; Gokden, N., et al., Diagnostic Cytopathology 36: 473-477, 2008). A subtractive hybridization strategy was used to look for genes whose expression decreased in Wilm's tumors in comparison to that in the normal kidney (Austruy, E., et al., Cancer Research 53: 2888-2894, 1993). Among 6 isolated clones examined in this study, one gene was characterized as encoding renal dipeptidase 1 (DPEP1), an apical membrane bound zinc metallopeptidase involved in the hydrolytic metabolism of dipeptides and glutathione (Austruy, E., et al., Cancer Research 53: 2888-2894, 1993). In addition, previous studies have found that transcript expression for both AQP1 and adipose differentiation-related protein (ADFP) decreased as tumor stage increased (Huang, Y., et al., Eur. Urol. 56: 690-698, 2009; Yao, M., et al., Clin. Cancer Res. 13: 152-160, 2007; Yao, M., et al. J. Pathol. 205: 377-387, 2005).

At present, there is no method for screening and diagnosis of renal cancer. There is no method for surveillance and detection of recurrence. The standard laboratory test for overall kidney function, measurement of serum creatinine levels, is widely considered not sensitive enough to detect kidney cancer.

SUMMARY

In view of these and other limitations of present methods, the present inventors realized that there is an unmet need for tests for detecting renal cancer.

Accordingly, the present inventors have developed methods for detecting, diagnosing or monitoring a renal cancer in a subject. In various embodiments, these methods comprise providing a biological fluid sample from the subject, and contacting the sample with at least one primary probe that binds at least one polypeptide which is present in the fluid at an elevated level in an individual having a renal cancer, under conditions sufficient for formation of a complex comprising the at least one probe and the at least one polypeptide if present. Detection and/or quantification of the complex can then be used to detect, diagnose or monitor a renal cancer. In some configurations, a subject can be deemed to have a renal cancer if the complex comprises at least one polypeptide at an elevated level compared to a control complex.

In various aspects of these methods, the at least one polypeptide can comprise a contiguous sequence of at least 4 amino acids, and can be a polypeptide marker of renal cancer. In some configurations, a polypeptide can be a polypeptide which is over-expressed in cells comprised by renal cancer tissue. A renal cancer can be, without limitation a clear cell carcinoma, a papillary carcinoma or a combination thereof.

In some aspects of the methods, the at least one polypeptide can be aquaporin-1 (AQP-1), a fragment thereof comprising a contiguous sequence of at least 4 amino acids of AQP-1, an adipose differentiation-related protein (ADFP) or a fragment thereof comprising a contiguous sequence of at least 4 amino acids of ADFP, paired box protein-2 (Pax-2) or a fragment thereof comprising a contiguous sequence of 4 amino acids of Pax-2.

In some aspects of the methods, the at least one polypeptide can be an exosomal protein or a fragment thereof comprising a contiguous sequence of at least 4 amino acids of an exosomal protein.

In various aspects of the methods, a biological fluid sample can be a blood sample, a serum sample, a plasma sample, a saliva sample or a urine sample of a subject, such as a human subject having, suspected of having, or at risk for developing a renal cancer. In some configurations, the fluid sample is a urine sample.

In various aspects of the present teachings, a probe can be without limitation, an antibody, an antigen-binding fragment of an antibody, an aptamer, or an avimer. In some embodiments, a probe can be an antibody or an antigen-binding fragment thereof, such as an Fab fragment. An antibody of the present teachings can be a polyclonal or a monoclonal antibody.

In various aspects, detecting presence, absence or quantity of a polypeptide can comprise any immunodetection method known to skilled artisans, such as, without limitation, an immunoprecipitation assay, an ELISA, a radioimmunoassay, a Western blot assay, a dip stick assay, or a bead assay.

In various aspects of the present teachings, a primary probe can comprise a label, and detecting presence, absence or quantity of a complex can comprise quantifying the label. A label of a probe in the various embodiments disclosed herein can be, without limitation, an enzyme, a radioisotope, a fluorogen, fluorophore, a chromogen or a chromophore. In various configurations, an enzyme can be any enzyme known to skilled artisans, such as, without limitation, a peroxidase, a phosphatase, a galactosidase or a luciferase; a radioisotope can be any radioisotope known to skilled artisans, such as, without limitation, a $^{32}P$, a $^{33}P$, $^{35}S$, a $^{14}C$, an $^{125}I$, an $^{131}I$ or a $^{3}H$; a fluorophore can be any fluorophore known to skilled artisans, such as, without limitation, a fluorescein, a rhodamine, an Alexa Fluor® (Invitrogen Corporation, Carlsbad, Calif.), an IRDye® (LI-COR Biosciences, Lincoln, Nebr.), a coumarin, an indocyanine or a quantum dot (Colton, H. M., et al., Toxicological Sciences 80: 183-192, 2004). In some configurations, a label can be, without limitation, a biotin, a digoxygenin, or a peptide comprising an epitope.

In various aspects of the present teachings, the methods can comprise a) contacting a sample with a solid surface that can bind at least one polypeptide that is elevated in an individual having a renal cancer; and b) subsequent to a), contacting the surface with at least one primary probe that binds the at least one polypeptide under conditions sufficient for formation of a complex comprising the at least one probe and the at least one polypeptide if present.

In various aspects of the present teachings, detecting presence, absence or quantity of a complex comprising a polypeptide and a primary probe can comprise contacting the complex with at least one secondary probe that binds the at least one primary probe under conditions sufficient for formation of a second complex comprising the at least one secondary probe, the at least primary probe and the at least one polypeptide if present, and detecting presence, absence or quantity of the second complex. In various configurations, a secondary probe can be, without limitation, an antibody directed against the at least one primary probe, an aptamer that binds the at least one primary probe, an avimer that binds the at least one primary probe, an avidin or a streptavidin. In various configurations, the at least one secondary probe can comprise a label described for a primary probe. Detection of the presence, absence or quantity of a second complex can comprise quantifying the label.

In various aspects, a polypeptide that is elevated in a subject having a renal cell cancer or a primary probe of the present teachings can be bound to a solid support. A solid support can have a solid surface to which a polypeptide or probe can bind. Without limitation, a solid support can be an ELISA plate, a bead, a dip stick, a test strip or a microarray. In various configurations, a bead can be a polystyrene bead, such as a magnetized polystyrene bead.

In some aspects, solid surface that can bind at least one polypeptide which is elevated in an individual having a renal cancer can comprise at least one probe (an "additional probe") that specifically binds the at least one polypeptide. A solid surface comprising such a probe can be used in a "sandwich" assay in which at least one polypeptide in a sample binds to the probe that is immobilized on the surface. A primary probe which binds the same at least one peptide can then be used to detect the at least one polypeptide bound to the solid surface. An additional probe of these aspects can be, without limitation, an antibody, an antigen-binding fragment of an antibody, an aptamer, or an avimer.

In some aspects of the present teachings the present inventors disclose methods of monitoring a renal cancer in a subject receiving a therapy for a renal cancer. In various embodiments, these methods comprise a) providing a plurality of biological fluid samples from a subject, each sample collected at a time before, during or after administration of a therapy; and b) for each sample: i) contacting the sample with at least one probe that binds at least one polypeptide which is present in the fluid at an elevated level in an individual having a renal cancer, under conditions sufficient for formation of a complex comprising the at least one probe and the at least one polypeptide if present; and ii) detecting quantity of the complex. By comparing quantities of complex between different samples, a skilled artisan can determine if a therapy is beneficial for treatment of a renal cell carcinoma, in that quantity of the complex will be reduced in samples obtained from a subject during or after receiving treatment, compared to samples from the same subject obtained at earlier times.

In some aspects of the present teachings the present inventors disclose methods of testing a candidate therapeutic method for effectiveness against a renal cancer. In various configurations, these methods can comprise a) providing a first biological fluid sample from each of one or more subjects; b) contacting each first sample with at least one probe that binds at least one polypeptide which is present in the fluid at an elevated level in an individual having a renal cancer, under conditions sufficient for formation of a first probe/antigen complex between the at least one polypeptide and the at least one probe; c) administering a candidate therapeutic method to the one or more subjects; d) providing a second biological fluid sample obtained subsequent to c) for each of the one or more subjects; e) contacting the second sample with the at least one probe under conditions sufficient for formation of a second probe/antigen complex between the at least one polypeptide and the at least one probe; and f) detecting presence, absence or quantity of the first complex and the second complex. In these methods, a candidate therapeutic method can be deemed effective against renal cancer if the quantity of a second complex is less than that of a first complex. In some configurations, a candidate therapeutic method can comprise administering to a subject a candidate pharmaceutical compound. In some embodiments, a pharmaceutical formulation can comprise a candidate pharmaceutical compound and can furthermore comprise an excipient.

In some aspects of the present teachings the present inventors disclose methods of detecting, diagnosing or monitoring a renal cancer in a subject. Methods of these aspects can comprise: providing a biological fluid sample from the subject; and determining by mass spectroscopy the presence, absence, quantity or identity in the sample of at least one polypeptide which is present in the fluid at an elevated level in an individual having a renal cancer. In some configurations, the present teachings include clinical applications such as, without limitation, specific diagnosis of renal clear cell or papillary cancer after discovery of an imaged renal mass, weighing treatment options (Benway, B. M., et al., Curr. Urol. Rep. 10: 11-16, 2009), Thus, a viable implementation of the disclosed methods can include widespread, annual (or other appropriate interval) population screening for renal cancer in, for example, at-risk populations. In some embodiments, measurement of urinary AQP1 and ADFP levels that produce negative test result can be clinically useful. For example, the current standard of care for a renal mass found during incidental radiologic examination is prompt nephrectomy because cancer is presumed. However, in some configurations, a negative finding from a test in accordance with the present teachings can be used by a clinician to reach a decision to avoid nephrectomy. In some aspects, on computed tomography, clear cell carcinomas and oncocytomas have overlapping features and can be difficult to distinguish (Herts, B. R. et al., Am. J. Roentgenol 178: 367-372, 2002). In some configurations, urinary AQP1 and/or ADFP levels Can be applied as a follow-up to a radiologic finding to help diagnose cancer vs benign renal tumor.

If the latter is found, an unnecessary nephrectomy may be obviated, or at least watchful waiting may be possible.

In some aspects of the present teachings the present inventors disclose methods of monitoring a renal cancer in a subject receiving a therapy for a renal cancer. In various aspects, these methods can comprise: a) providing a plurality of biological fluid samples from a subject, each sample collected at a time before, during or after administration of a therapy; b) for each sample: determining by mass spectroscopy the presence, absence, quantity or identity in the sample of at least one polypeptide which is present in the fluid at an elevated level in an individual having a renal cancer; and c) comparing presence, absence, quantity or identity of the at least one polypeptide in 2 or more samples. A reduction over time in the amount of at least one such polypeptide in samples collected from a subject receiving a therapy can be indicative of a beneficial effect of the therapy.

In some aspects, the present inventors disclose methods for testing effectiveness of a candidate therapeutic process for treatment of a renal cancer. In various embodiments, these methods comprise a) providing a first biological fluid sample from each of one or more subjects; b) administering a candidate therapeutic process to the one or more subjects; c) providing one or more second biological fluid samples obtained subsequent to b) for each of the one or more subjects; and d) for each sample, determining by mass spectroscopy the presence, absence, quantity or identity in the sample of at least one polypeptide which is present in the fluid at an elevated level in an individual having a renal cancer, whereby the candidate therapeutic process can be deemed effective against renal cancer if the quantity of the at least one polypeptide in a second sample of one or more subjects is less than that of a first sample. In some configurations of these methods, a candidate therapeutic process can comprise administering a candidate pharmaceutical compound to the one or more subjects.

In various aspects, the present teachings include an aqueous mixture comprising a complex. In various configurations, a complex can comprise a body fluid sample comprising at least one polypeptide which is present at an elevated level in an subject having a renal cancer compared to an individual who does not have a renal cancer, and at least one primary probe that binds the at least one polypeptide. In various configurations, the body fluid can be any body fluid, such as, without limitation, blood, serum plasma, saliva, or urine. In some embodiments, the at least one polypeptide can be at an elevated level compared to that of a control, i.e., the body fluid of an individual who does not have a renal cancer. In various configurations, the at least one polypeptide can be, without limitation, aquaporin-1 (AQP-1), a fragment thereof comprising a contiguous sequence of at least 4 amino acids of AQP-1, an adipose differentiation-related protein (ADFP), a fragment thereof comprising a contiguous sequence of at least 4 amino acids of ADFP, paired box protein-2 (Pax-2) or a fragment thereof comprising a contiguous sequence of 4 amino acids of Pax-2. In addition, in various configurations, the at least one probe can be an antibody or antigen-binding fragment thereof, directed against at least one polypeptide selected from aquaporin-1 (AQP-1), an adipose differentiation-related protein (ADFP), or paired box protein-2 (Pax-2).

Hence, in various configurations of the present teachings, the body fluid sample of a mixture can be a urine sample; the at least one polypeptide can be urinary AQP-1, urinary ADFP or urinary Pax-2, and the at least one primary probe can be an anti-AQP-1 antibody, an anti-ADFP antibody, or an anti-Pax-2 antibody, respectively. Furthermore, the complex can be at an elevated level when the urine sample is from a subject having a renal cell cancer, compared to that of a control, i.e., a urine sample from an individual who does not have renal cancer.

The present teachings includes the following aspects.

1. A method of detecting, diagnosing or monitoring a renal cancer in a subject, the method comprising:
   providing a biological fluid sample from the subject; and
   contacting the sample with at least one primary probe that binds at least one polypeptide which is present in the fluid at an elevated level in an individual having a renal cancer, under conditions sufficient for formation of a primary complex comprising the at least one primary probe and the at least one polypeptide if present; and
   detecting presence, absence or quantity of the complex.

2. A method of detecting, diagnosing or monitoring a renal cancer in accordance with aspect 1, wherein the subject is deemed to have renal cancer if the complex comprises the at least one polypeptide at an elevated level compared to a control complex.

3. A method of detecting, diagnosing or monitoring a renal cancer in accordance with aspect 1, wherein the renal cancer is selected from the group consisting of a clear cell carcinoma, a papillary carcinoma or a combination thereof.

4. A method of detecting, diagnosing or monitoring a renal cancer in accordance with aspect 1, wherein the at least one polypeptide comprises a contiguous sequence of at least 4 amino acids.

5. A method of detecting, diagnosing or monitoring a renal cancer in accordance with aspect 1, wherein the at least one polypeptide is a polypeptide marker of renal cancer.

6. A method of detecting, diagnosing or monitoring a renal cancer in accordance with aspect 5, wherein the polypeptide marker is a polypeptide over-expressed in cells comprised by renal cancer tissue.

7. A method of detecting, diagnosing or monitoring a renal cancer in accordance with aspect 1, wherein the at least one polypeptide is selected from the group consisting of aquaporin-1 (AQP-1), a fragment thereof comprising a contiguous sequence of at least 4 amino acids of AQP-1, an adipose differentiation-related protein (ADFP), a fragment thereof comprising a contiguous sequence of at least 4 amino acids of ADFP, paired box protein-2 (Pax-2) and a fragment thereof comprising a contiguous sequence of 4 amino acids of Pax-2.

8. A method of detecting, diagnosing or monitoring a renal cancer in accordance with aspect 1, wherein the at least one polypeptide is an exosomal protein a fragment thereof comprising a contiguous sequence of at least 4 amino acids of an exosomal protein.

9. A method of detecting, diagnosing or monitoring a renal cancer in accordance with aspect 1, wherein the fluid sample is selected from the group consisting of a blood sample, a serum sample, a plasma sample, a saliva sample and a urine sample.

10. A method of detecting, diagnosing or monitoring a renal cancer in accordance with aspect 1, wherein the fluid sample is a urine sample.

11. A method of detecting, diagnosing or monitoring a renal cancer in accordance with aspect 1, wherein the at least one primary probe is selected from the group consisting of an antibody, an antigen-binding fragment of an antibody, an aptamer, and an avimer.

12. A method of detecting, diagnosing or monitoring a renal cancer in accordance with aspect 1, wherein the at least one primary probe is an antibody or an antigen-binding fragment thereof.

13. A method of detecting, diagnosing or monitoring a renal cancer in accordance with aspect 12, wherein the antibody is a polyclonal antibody or a monoclonal antibody.

14. A method of detecting, diagnosing or monitoring a renal cancer in accordance with aspect 12, wherein the detecting comprises an immunoprecipitation assay, an ELISA, a radioimmunoassay, a Western blot assay, a dip stick assay, or a bead assay.

15. A method of detecting, diagnosing or monitoring a renal cancer in accordance with aspect 12, wherein the detecting comprises an ELISA assay or a Western blot assay.

16. A method of detecting, diagnosing or monitoring a renal cancer in accordance with aspect 1, wherein the at least one primary probe comprises a label, and the detecting presence, absence or quantity of the complex comprises quantifying the label.

17. A method of detecting, diagnosing or monitoring a renal cancer in accordance with aspect 16, wherein the label is selected from the group consisting of an enzyme, a radioisotope, a fluorogen, fluorophore, a chromogen and a chromophore.

18. A method of detecting, diagnosing or monitoring a renal cancer in accordance with aspect 17, wherein the enzyme is selected from the group consisting of a peroxidase, a phosphatase, a galactosidase and a luciferase.

19. A method of detecting, diagnosing or monitoring a renal cancer in accordance with aspect 17, wherein the radioisotope is selected from the group consisting of a $^{32}P$, a $^{33}P$, $^{35}S$, a $^{14}C$, an $^{125}I$, an $^{131}I$ and a $^{3}H$.

20. A method of detecting, diagnosing or monitoring a renal cancer in accordance with aspect 17, wherein the fluorophore is selected from the group consisting of a fluorescein, a rhodamine, an Alexa Fluor®, an IRDye®, a coumarin, an indocyanine and a quantum dot.

21. A method of detecting, diagnosing or monitoring a renal cancer in accordance with aspect 16, wherein the label is selected from the group consisting of a biotin, a digoxygenin, and a peptide comprising an epitope.

22. A method of detecting, diagnosing or monitoring a renal cancer in accordance with aspect 1, wherein the contacting comprises:
    a) contacting the sample with a solid surface that binds the at least one polypeptide; and
    b) subsequent to a), contacting the surface with the at least one primary probe.

23. A method of detecting, diagnosing or monitoring a renal cancer in accordance with aspect 1, wherein the detecting presence, absence or quantity of the complex comprises contacting the complex with at least one secondary probe that binds the at least one primary probe under conditions sufficient for formation of a second complex comprising the at least one secondary probe, the at least primary probe and the at least one polypeptide if present; and
    d) detecting presence, absence or quantity of the second complex.

24. A method of detecting, diagnosing or monitoring a renal cancer in accordance with aspect 23, wherein the at least one secondary probe is selected from the group consisting of an antibody directed against the at least one primary probe, an aptamer that binds the at least one primary probe, an avimer that binds the at least one primary probe, an avidin and a streptavidin.

25. A method of detecting, diagnosing or monitoring a renal cancer in accordance with aspect 23, wherein the at least one secondary probe comprises a label, and the detecting presence, absence or quantity of the second complex comprises quantifying the label.

26. A method of detecting, diagnosing or monitoring a renal cancer in accordance with aspect 25, wherein the label is selected from the group consisting of an enzyme, a radioisotope, a fluorogen, fluorophore, a chromogen and a chromophore.

27. A method of detecting, diagnosing or monitoring a renal cancer in accordance with aspect 26, wherein the enzyme is selected from the group consisting of a peroxidase, a phosphatase, a galactosidase and a luciferase.

28. A method of detecting, diagnosing or monitoring a renal cancer in accordance with aspect 26, wherein the radioisotope is selected from the group consisting of a $^{32}P$, a $^{33}P$, $^{35}S$, a $^{14}C$, an $^{125}I$, an $^{131}I$ and a $^{3}H$.

29. A method of detecting, diagnosing or monitoring a renal cancer in accordance with aspect 26, wherein the fluorophore is selected from the group consisting of a fluorescein, a rhodamine, an ALEXA FLUOR® fluorophore, an IRDYE® fluorophore, a coumarin, an indocyanine and a quantum dot.

30. A method of detecting, diagnosing or monitoring a renal dancer in accordance with aspect 25, wherein the label is selected from the group consisting of a biotin, a digoxygenin, and a peptide comprising an epitope.

31. A method of detecting, diagnosing or monitoring a renal cancer in accordance with aspect 1, wherein the at least one primary probe is bound to a polystyrene bead.

32. A method of detecting, diagnosing or monitoring a renal cancer in accordance with aspect 31, wherein the polystyrene bead is a magnetized polystyrene bead.

33. A method of detecting, diagnosing or monitoring a renal cancer in accordance with aspect 23, wherein the at least one secondary probe is bound to a polystyrene bead.

34. A method of detecting, diagnosing or monitoring a renal cancer in accordance with aspect 33, wherein the polystyrene bead is a magnetized polystyrene bead.

35. A method of detecting, diagnosing or monitoring a renal cancer in accordance with aspect 22, wherein the solid surface is selected from the group consisting of an ELISA plate, a bead, a dip stick, a test strip and a microarray.

36. A method of detecting, diagnosing or monitoring a renal cancer in accordance with aspect 22, wherein the solid surface that binds the at least one polypeptide comprises at least one additional probe that specifically binds the at least one polypeptide.

37. A method of detecting, diagnosing or monitoring a renal cancer in accordance with aspect 36, wherein the at least one additional probe that specifically binds the at least one polypeptide is selected from the group consisting of an antibody, an antigen-binding fragment of an antibody, an aptamer, and an avimer.

38. A method of monitoring a renal cancer in a subject receiving a therapy for a renal cancer, comprising:
    a) providing a plurality of biological fluid samples from a subject, each sample collected at a time before, during or after administration of a therapy; and
    b) for each sample: i) contacting the sample with at least one probe that binds at least one polypeptide which is present in the fluid at an elevated level in an individual having a renal cancer, under conditions sufficient for formation of a complex comprising the at least one probe and the at least one polypeptide if present; and ii) detecting quantity of the complex; and
    d) comparing quantities of 2 or more complexes.

39. A method in accordance with aspect 38, wherein the comparing quantities of 2 or more complexes comprises determining a benefit from the therapy if the quantity of the complex in a sample is less than that of a sample collected at a prior time.

40. A process for testing a candidate therapeutic method for effectiveness against a renal cancer, the process comprising:
    a) providing a first biological fluid sample from each of one or more subjects;
    b) contacting each first sample with at least one probe that binds at least one polypeptide which is present in the fluid at an elevated level in an individual having a renal cancer, under conditions sufficient for formation of a first probe/antigen complex between the at least one polypeptide and the at least one probe;
    c) administering a candidate therapeutic method to the one or more subjects;
    d) providing a second biological fluid sample obtained subsequent to c) for each of the one or more subjects;
    e) contacting the second sample with the at least one probe under conditions sufficient for formation of a second probe/antigen complex between the at least one polypeptide and the at least one probe; and
    f) detecting presence, absence or quantity of the first complex and the second complex,
whereby the candidate therapeutic method is deemed effective against renal cancer if the quantity of the second complex is less than that of the first complex.

41. A process for testing a candidate therapeutic method for effectiveness against a renal cancer in accordance with aspect 40, wherein the candidate therapeutic method comprises administering to the subject a candidate pharmaceutical compound.

42. A method of detecting, diagnosing or monitoring a renal cancer in a subject, the method comprising:
providing a biological fluid sample from the subject; and
determining by mass spectroscopy the presence, absence, quantity or identity in the sample of at least one polypeptide which is present in the fluid at an elevated level in an individual having a renal cancer.

43. A method of monitoring a renal cancer in a subject receiving a therapy for a renal cancer, comprising:
a) providing a plurality of biological fluid samples from a subject, each sample collected at a time before, during or after administration of a therapy;
b) for each sample: determining by mass spectroscopy the presence, absence, quantity or identity in the sample of at least one polypeptide which is present in the fluid at an elevated level in an individual having a renal cancer; and
c) comparing presence, absence, quantity or identity of the at least one polypeptide in 2 or more samples.

44. A method in accordance with aspect 43 wherein the comparing presence, absence, quantity or identity of the at least one polypeptide in 2 or more samples comprises determining a benefit from the therapy if the quantity of the polypeptide in a sample is less than that of a sample collected at a prior time.

45. A method for testing effectiveness of a candidate therapeutic process for treatment of a renal cancer, the method comprising:
a) providing a first biological fluid sample from each of one or more subjects;
b) administering a candidate therapeutic method to the one or more subjects;
c) providing one or more second biological fluid samples obtained subsequent to b) for each of the one or more subjects; and
d) for each sample, determining by mass spectroscopy the presence, absence, quantity or identity in the sample of at least one polypeptide which is present in the fluid at an elevated level in an individual having a renal cancer,
whereby the candidate therapeutic method is deemed effective against renal cancer if the quantity of the at least one polypeptide in a second sample of one or more subjects is less than that of a first sample.

46. A method in accordance with aspect 45, wherein the candidate therapeutic process comprises administering a candidate pharmaceutical compound to the one or more subjects.

47. An aqueous mixture comprising a complex, the complex comprising:
a) a body fluid sample comprising at least one polypeptide which is present at an elevated level in an subject having a renal cancer compared to an individual who does not have a renal cancer; and
b) at least one primary probe that binds the at least one polypeptide.

48. A mixture in accordance with aspect 47, wherein the body fluid sample is selected from the group consisting of a blood sample, serum sample, a plasma sample, a saliva sample, and a urine sample.

49. A mixture in accordance with aspect 47, wherein the body fluid sample is a urine sample.

50. A mixture in accordance with aspect 47, wherein the body fluid sample comprises the at least one polypeptide at an elevated level compared to that of an individual who does not have a renal cancer.

51. A mixture in accordance with aspect 47, wherein the at least one polypeptide is selected from the group consisting of aquaporin-1 (AQP-1), a fragment thereof comprising a contiguous sequence of at least 4 amino acids of AQP-1, an adipose differentiation-related protein (ADFP), a fragment thereof comprising a contiguous sequence of at least 4 amino acids of ADFP, paired box protein-2 (Pax-2) and a fragment thereof comprising a contiguous sequence of 4 amino acids of Pax-2.

52. A mixture in accordance with aspect 47, wherein the at least one probe is an antibody or antigen-binding fragment thereof, directed at against at least one polypeptide selected from the group consisting of aquaporin-1 (AQP-1), a fragment thereof comprising a contiguous sequence of at least 4 amino acids of AQP-1, an adipose differentiation-related protein (ADFP), a fragment thereof comprising a contiguous sequence of at least 4 amino acids of ADFP, paired box protein-2 (Pax-2) and a fragment thereof comprising a contiguous sequence of 4 amino acids of Pax-2.

53. A mixture in accordance with aspect 50, wherein the body fluid sample is a urine sample, the at least one polypeptide is urinary AQP-1 and the at least one primary probe is an anti-AQP-1 antibody.

54. A mixture in accordance with aspect 50, wherein the body fluid sample is a urine sample, the at least one polypeptide is urinary ADFP and the at least one primary probe is an anti-ADFP antibody.

55. A mixture in accordance with aspect 50, wherein the body fluid sample is a urine sample, the at least one polypeptide is urinary Pax-2 and the at least one primary probe is an anti-Pax-2 antibody.

DETAILED DESCRIPTION

Figure 1:
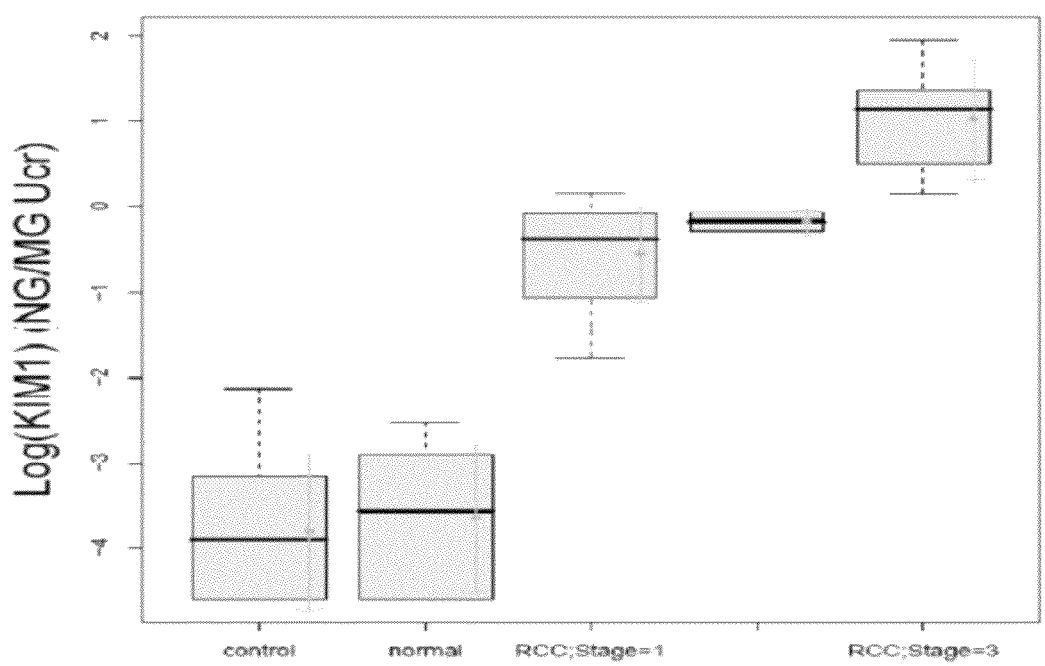
FIG. 1 illustrates Log urinary KIM-1 factored by tumor stage.

The present inventors have developed methods of detecting renal cell carcinomas in a subject, such as a human who has, is suspected of having, or is at risk of developing a renal cancer, such as, without limitation, a smoker or a person exposed to a solvent such as trichloroethylene. These methods, in various configurations, are applicable to humans, and can be used for early and non-invasive detection of renal cancer, population screening for renal cancer, post-treatment surveillance for recurrence of renal cancer, as well as progression, regression or time-course of disease in untreated, partially treated, and definitively treated patients with renal cancer. In various configurations, the methods can be non-invasive, and can use biological fluids such as urine or blood, and in some embodiments, urine. Furthermore, in various embodiments, the methods can be relatively inexpensive and permit high through-put and/or point-of-care testing assays to screen at risk populations or individuals for kidney cancers. For example, in some configurations, treatment success or failure can be monitored in individuals diagnosed with kidney cancer. Furthermore, in various embodiments, the methods can be used for large-scale population screening and/or surveillance.

The present inventors have found that urine concentrations of AQP1 and ADFP are significantly increased in patients with clear cell or papillary carcinoma compared with concentrations in a control group of patients undergoing nonnephrectomy surgery, a control group of healthy volunteers, and patients with oncocytoma (benign medullary tumor). The AQP1 and ADFP concentrations diminished significantly after tumor removal (postnephrectomy group), a pseudocontrol, demonstrating the renal tumor origin of these urine proteins. Postoperative AQP1 and ADFP concentrations in the nonnephrectomy surgical patients were unchanged from preoperative concentrations, showing that the postoperative change in the patients with renal cancer was not an artifact of anesthesia or surgery. Accordingly, diagnosis of renal clear cell and papillary cancers can comprise determining urine concentrations (normalized to creatinine excretion) of the proteins AQP1 and ADFP. These proteins can be sensitive, specific, and noninvasive biomarkers for the diagnosis of renal clear cell and papillary cancers. The AQP1 concentrations can reflect tumor burden, estimated from excised tumor size. In addition, gene expression may not be a parallel indicator of anticipated protein expression. Oncocytomas, which account for a small fraction (5%) of renal cancers and which arise from collecting duct cells, were not associated with increased AQP1 and ADFP elimination. Of note, patients who had renal masses diagnosed by incidental radiologic findings or clinical symptoms but who did not have cancers of the proximal tubule had normal urine AQP1 and ADFP excretion.

In some configurations, Western blot analysis using antibodies against AQP-1 and ADFP can show that urine concentrations of these polypeptides are significantly increased in patients diagnosed with clear cell and papillary carcinoma of the kidney, in comparison to normal patients without kidney cancer. Furthermore, in some configurations, Western blot analysis using antibodies against AQP-1 and ADFP can show that upon surgical excision of a kidney tumor, urinary concentrations of these proteins can decline postoperatively.

In various configurations, the methods comprise obtaining a body fluid sample from a subject, and assaying the sample for the presence, absence and/or quantity of a polypeptide or a fragment thereof comprising at least four contiguous amino acids, wherein the polypeptide or fragment thereof is elevated in a body fluid of persons having a kidney cancer, compared to the same type of body fluid in a control sample such as a sample from a person who does not have a renal cancer. In some embodiments, the body fluid sample can be a urine sample.

In some embodiments, a polypeptide or fragment thereof can be, without limitation, an Aquaporin-1 polypeptide (AQP-1), a fragment thereof comprising a contiguous sequence of at least 4 amino acids of AQP-1, an adipose differentiation-related protein (ADFP), a fragment thereof comprising a contiguous sequence of at least 4 amino acids of ADFP, a paired box protein-2 (Pax-2), or a fragment thereof comprising a contiguous sequence of at least 4 amino acids of Pax-2. An aquaporin-1 (AQP-1) can have an amino acid sequence as set forth as SEQ ID NO: 1, or can be a naturally occurring allelic variant thereof. This sequence has a REFSEQ accession number of NM_198098.1. An adipose differentiation-related protein (ADFP) can have an amino acid sequence set forth as SEQ ID NO: 2, or can be a naturally occurring allelic variant thereof. This sequence has a REFSEQ accession number of NM_001122.2. A paired box protein-2 (Pax-2) can be any naturally occurring isoform of Pax-2, such as Pax-2 isoform a, isoform h, isoform c, isoform d, isoform d, or isoform e. These isoforms can have an amino acid sequence set forth as SEQ ID NO: 3, SEQ ID NO: 4, SEQ ID NO: 5, SEQ ID NO: 6, and SEQ ID NO: 7, respectively. These sequences have REFSEQ accession numbers of NP_003978, NP_000269, NP_003979, NP_003980 and NP_003981, respectively.

In various aspects, detection and quantification of a polypeptide or a fragment thereof comprised by a body fluid can comprise detecting the polypeptide using a probe that specifically binds the polypeptide or fragment thereof. Any probe-based method of detecting and/or quantifying a polypeptide can be used to practice the methods of these aspects. Types of probes that can be used include, without limitation, an antibody, an antigen binding domain or fragment of an antibody such as an Fab fragment, an aptamer (Jayasena, S. D., et al., Clinical Chemistry 45: 1628-1650, 1999), an avimer (Silverman, J., et al., Nature Biotechnology 23: 1556-1561, 2005) or any combination thereof. An antibody of the present teachings can be a polyclonal or a monoclonal antibody. Antibodies can be generated using standard methods known to skilled artisans. An antibody can be used unconjugated, or conjugated with a label such as, for example, a fluorophore or a chromophore. An unlabelled antibody can be conjugated using conjugation methods known to skilled artisans. In some configurations, an antibody can be obtained from a commercial supplier, either unconjugated or conjugated with a label. For example, an anti-AQP-1 antibody can be rabbit anti-AQP-1 polyclonal antibody available from Abcam (Cambridge, Mass.), catalog ab65837; a mouse anti-AQP-1 monoclonal antibody, clone 7d11, available from Thermo Fisher Scientific (Rockford, Ill.) catalog MA1-24915; or a mouse anti-AQP-1 monoclonal antibody, clone 3h550, available from LifeSpan Biosciences, Inc. (Seattle, Wash.) catalog LS-C3792-100. An anti-ADFP antibody can be, for example, rabbit anti-ADFP polyclonal antibody available from Abcam (Cambridge, Mass.), catalog ab52355; a mouse anti-ADFP monoclonal antibody, clone AP125 available from ARP American Research Products, Inc. (Belmont, Mass.), catalog 03-610102; or an FITC-conjugated mouse anti-ADFP monoclonal antibody, clone AP125 available from ARP American Research Products, Inc. (Belmont, Mass.), catalog 03-614102. An anti-Pax-2 antibody can be, for example, a rabbit anti-Pax-2 polyclonal antibody, available from LifeSpan Biosciences, Inc. (Seattle, Wash.) catalog LS-C61801 or LS-C31501; or a mouse anti-Pax-2 monoclonal antibody, clone 3C7, available from Sigma-Aldrich (Saint Louis, Mo.) catalog WH0005076M1.

The present inventors disclose herein their findings that the urine of patients with kidney cancer contains a variety of proteins found at increased levels compared to the urine of normal subjects, i.e., individuals who do not have renal cancer. Such proteins can be used as biomarkers for diagnosing and/or monitoring kidney cancers. Additionally, the inventors disclose that urinary exosomes are a rich and concentrated source for polypeptides that can be used as biomarkers for both normal and tumor cells of the kidney.

In various aspects, the methods can comprise using at least one probe that specifically recognizes and binds at least one polypeptide or a fragment thereof that is elevated in a body fluid of a subject having a renal cell carcinoma, to quantify such polypeptides or fragments. Detection of an elevated polypeptide or fragment thereof can be diagnostic of a kidney cancer. Furthermore, the present methods can include monitoring a subject diagnosed with a kidney cancer for responses to a therapy.

In various aspects of the disclosed methods, a probe can comprise a label. In some configurations, when the label is a chromophore, the label can be any chromophore known to skilled artisans, such as, without limitation, a dichlorotriazine dye such as 1-Amino-4-[3-(4,6-dichlorotriazin-2-ylamino)-4-sulfophenylamino]anthraquinone-2-sulfonic acid (PROCION BLUE MX-R® (Fluka AG, Switzerland)) (Reactive Blue 4). Such labels can be detected by methods known to skilled artisans, such as measurement of optical absorbance using a spectrophotometer.

In some configurations, when the label is a fluorophore, the label can be any fluorophore known to skilled artisans, such as, without limitation, a fluorescein, a rhodamine, an ALEXA FLUOR® (Invitrogen Corporation, Carlsbad, Calif.) fluorophore, an IRDYE® (LI-COR Biosciences, Lincoln, Nebr.) fluorophore, a coumarin, an indocyanine or a quantum dot (Colton, H. M., et al., Toxicological Sciences 80: 183-192, 2004). Such labels can be detected by methods known to skilled artisans, such as measurement of fluorescence using a fluorometer or scanner.

In some configurations, when the label is a radioisotope, the radioisotope can be any radioisotope known to skilled artisans, such as, without limitation, a $^{32}P$, a $^{33}P$, $^{35}S$, a $^{14}C$, an $^{125}I$, an $^{131}I$, or a $^{3}H$. A radioisotope can be detected by any detection method known to skilled artisans, such as, without limitation, detection with a scintillation counter or by exposure of photographic film.

In some configurations, when the label is an enzyme, a method of these aspects can further comprise adding to the mixture a substrate of the enzyme, and detecting presence and/or quantity of a product of a reaction between the enzyme and the substrate.

An enzyme of these configurations can be any enzyme for which a substrate is available. Examples of such enzymes include, without limitation, a peroxidase such as a horseradish peroxidase, a phosphatase such as an alkaline phosphatase, a galactosidase such as a β-galactosidease, and a luciferase, such as a firefly luciferase. In some configurations, a substrate can be a chromogen or a fluorogen, or can yield a chemiluminescent product. If the substrate is a chemiluminescent substrate, qualititative and/or quantitative detection of the enzyme can comprise visual assessment, and/or measuring light produced as a product of a reaction between the substrate and the enzyme. For example, if the enzyme is an alkaline phosphatase, the substrate can be a chemiluminescent substrate such as CDP-Star® (Sigma-Aldrich Chemical Co., St, Louis, Mo.). In another example, if the enzyme is a luciferase, the substrate can be a luciferin.

If the substrate is a chromogenic substrate, qualititative and/or quantitative detection of the enzyme can comprise visual assessment, and/or measuring optical absorbance of the reaction product, such as, without limitation, measuring absorbance between 390 and 410 nm when the enzyme is an alkaline phosphatase and the substrate is dinitrophenyl phosphate or horse radish peroxidase when the substrate is tetramethylbenzidine. If the substrate is a fluorogenic substrate, qualititative and/or quantitative detection of the enzyme can comprise visual assessment, and/or measuring fluorescent light intensity using a fluorometer or scanner.

In some configurations, when the label is a probe-binding target, the probe-binding target can be any molecular target for a probe, such as, without limitation, a ligand to which a probe binds, such as, without limitation, an antigen to which an antibody binds. In various configurations of these methods, a probe-binding target can be, without limitation, a biotin, a digoxygenin, or a peptide, and a probe for the probe-binding target can be, without limitation, an avidin, a streptavidin, an anti-biotin antibody, an anti-digoxygenin antibody, or a peptide antibody directed against a peptide. Accordingly, in various configurations of these methods, a label and a probe can be, without limitation, a) a biotin and an avidin, b) a biotin and a streptavidin, c) a biotin and an anti-biotin antibody, d) a digoxygenin and an anti-digoxygenin antibody, or e) a peptide and an antibody directed against the peptide.

In some configurations, the at least one antibody can be detected with a secondary antibody. Accordingly, the at least one antibody can be, without limitation, a mouse monoclonal antibody and the secondary antibody can be an antibody directed against a mouse immunoglobulin. In other configurations, a primary probe can be a polyclonal antibody such as a rabbit polyclonal antibody or a goat polyclonal antibody, and the secondary antibody can be an antibody directed against rabbit or goat immunoglobulins. In other configurations, a secondary probe can be a non-species-specific immunoglobulin binding protein such as Protein A. In various configurations, the secondary probe can comprise a label such as those a label described herein for a primary antibody.

In some configurations, the at least one antibody can be detected with a secondary antibody conjugated to polystyrene or magnetized polystyrene beads singly or in multiplex.

Methods and compositions described herein utilize laboratory techniques well known to skilled artisans. Such techniques can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999; and Sioud, M., ed. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used herein, the singular forms "a", "an" and "the" are intended to include the plural forms as well, unless the context indicates otherwise.

In addition, in some aspects of the present teachings including the Examples set forth below, analysis of proteins in body fluids such as urine can include the following materials and methods.

Investigational protocols disclosed herein were approved by the Washington University Institutional Review Board, and all patients gave written informed consent to participate. The protocol design was a prospective cohort study that included nested case cohorts, using a 2>2×1 design. One group was patients with a renal mass and presumptive diagnosis of renal cancer (n=42), a second group was patients undergoing nonnephrectomy (typically orthopedic) surgery but was selected to closely match the nephrectomy group by age and sex (n=15), and the third group was healthy volunteers (n=19) who provided spontaneously voided spot urine samples. In the nephrectomy group, urine samples were obtained (1) on the day of surgery before nephrectomy (preexcision, reflecting disease) and (2) at the time of a scheduled postsurgical follow-up visit (after excision, typically 1-3 months postoperatively, as a pseudocontrol). Patients who underwent nephrectomy served as their own controls, and comparison of prenephrectomy and postnephrectomy urine samples (Wilcoxon signed rank test) would be expected to reflect the presence or absence of specific tumor proteins excreted in the urine or a significant change in the abundance of normal urinary proteins modified by tumor presence. In the nonnephrectomy patients, urine samples were obtained (1) on the day of surgery and (2) at the time of a scheduled postsurgical follow-up. Follow-up averaged 27 days for the patients with kidney cancer and 32 days for the surgical control patients. Comparison of day of surgery and postoperative urine samples (Wilcoxon signed rank test) in the nonnephrectomy patients controlled for any effects of perioperative events on potential biomarker excretion. We compared the prenephrectomy with the nonnephrectomy urine samples (Wilcoxon rank sum test). We also compared the prenephrectomy urine samples to the healthy volunteers' urine samples (Wilcoxon rank sum test). Comparison of prenephrectomy urine and day of surgery urine samples in nonnephrectomy patients provided an additional evaluation of potential renal cancer biomarkers, whereas comparison of urine from healthy volunteers with that of the prenephrectomy urine samples assessed potential renal cancer biomarker excretion and determined a random population baseline level of biomarker.

Pathology reports obtained postoperatively provided renal tumor type (clear cell, papillary, oncocytoma, or chromophobe), size, grade and stage (TNM), or other diagnosis. Pertinent medical history, age, and sex were recorded, and serum creatinine level was used to calculate the estimated glomerular filtration rate (eGFR) by the Modification of Diet in Renal Disease equation (Levey, A. S., et al., Ann. Intern. Med. 130: 461-470, 1999).

The 42 patients with a presurgical presumptive diagnosis of kidney cancer were postoperatively determined to have clear cell carcinoma (n=22), papillary (chromatophilic) carcinoma (n=10), oncocytoma (n=4), and chromophobe renal cell carcinoma (n=1) on the basis of histologic analysis of the excised specimens, and 5 were found to have nonmalignant disease, including cystic nephroma, hemangioma, and plasmacytoma. Of the 32 patients with clear cell and papillary tumors, 24 had stage T1 disease without nodal or metastatic involvement, 2 had stage T2 disease, and 6 had stage T3 tumors. One patient with a T3 tumor had metastatic disease; otherwise, no other metastases or node involvement was noted. Postoperative urine samples were obtained in 15 patients with clear cell carcinoma, 10 with papillary carcinoma, 4 with oncocytoma, the 5 patients with nonmalignant disease, and the 15 nonnephrectomy surgical patients. Seven patients diagnosed as having clear cell kidney cancer, including the one patient with chromophobe renal cell carcinoma and 2 with other nonmalignant disorders, were lost to follow-up.

Urine Analysis

In some analyses, urine was centrifuged (1800 g for 10 minutes) to remove debris and was mixed with a protease inhibitor tablet (Roche Diagnostics, Indianapolis, Ind.) before processing for Western blot analysis or freezing at −80° C. Urinary creatinine concentration was quantified by the Jaffe reaction (Cockcroft, D. W., et al., Nephron 16: 31-41, 1976). Protein from 100 µL of fresh spun urine was precipitated with 1.5 mL of ice cold acetone-methanol (1:1), centrifuged, and washed with fresh acetone-methanol (1.5 mL). Precipitated proteins were dissolved in an amount of sodium dodecyl sulfate sample buffer such that 5 µL of sample reflected the amount of urine containing 10 µg of creatinine. Urine samples processed for Western blot were stored at 4° C. before analysis. The blocked membranes were incubated with 1:500 dilution of anti-AQP1 (H-55) antibody or a 1:200 dilution of anti-AD:FP (H-80) antibody (both from Santa Cruz Biotechnology Inc, Santa Cruz, Calif.) in blocking buffer that contained 0.1% Tween-20 overnight. After washing, the membranes were incubated with a 1:2000 dilution of donkey anti-rabbit IgG IRDye 680 (LICOR Biosciences, Lincoln, Nebr.) in blocking buffer with 0.1% Tween-20 for 1 hour. Both AQP1 and ADFP were visualized and quantified using an infrared imager (Odyssey Infrared Imager; LI-COR) and proprietary software. Both AQP1 and ADFP were quantified using arbitrary absorbance units. On each gel, the same 2 preexcision urine samples were analyzed and used to normalize the signal response across all gels run within the same or different days. During the span of 11 gels for AQP1, the variation in the signal of these common samples was 10%, and of 10 gels for ADFP, the variation was 9%.

Statistical Analyses

The Fisher exact test was used to compare sex ratios, smoking status, and eGFRs between groups independently. Analysis of variance was implemented to compare the age of study participants among groups. The urinary AQP1 and ADFP levels are summarized as means±SDs. The prenephrectomy and postnephrectomy urine samples were compared by the Wilcoxon signed rank test. The Wilcoxon rank sum test and the Kruskal-Wallis test were implemented correspondingly to analyze the differences between and among groups in urinary AQP1 or ADFP levels and also the eGFR, under the consideration of normality and small sample size. Relationships between tumor size and biomarker excretion were evaluated by regression analysis with Spearman rank correlation coefficients reported. Receiver operating characteristic (ROC) curve analysis was implemented to examine the predictive ability of AQP1 and ADFP in detecting renal cancer (clear cell and papillary) from surgical control through logistic regression modeling. Areas under the ROC curve were reported. All tests were 2-sided at a 0.05 significance level. Analyses were performed using SAS statistical software, version 9.2 (SAS Institute, Cary, N.C.) and Sigma Stat 3.5 (Systat Software, Point Richmond, Calif.).

EXAMPLES

The following non-limiting examples are provided to further illustrate the present teachings. Those of skill in the art should, in light of the present disclosure, appreciate that many changes can be made in the specific embodiments that are disclosed and still obtain a like or similar result without departing from the spirit and scope of the present teachings.

Example 1

This example illustrates determining suitability of biomarkers.

In this example, patients having surgery with a diagnosis of suspected renal carcinoma discovered, for the most part, as incidentalomas were recruited. We first determined the concentrations of two markers of kidney injury, Neutrophil gelatinase-associated lipocalin (NGAL) and kidney injury molecule-1 (KIM-1), in an IRB-approved study to ascertain their suitability to detect patients with kidney cancer. These two markers were measured since both NGAL and KIM-1 represent newly described biomarkers for the measure of acute and chronic kidney injury and would determine the suitability of using NGAL or KIM-1 to screen for kidney cancer. These proteins were measured by ELISAs using Duo-See kits from R&D Systems (Minneapolis, Minn.) for Lipocalin-2/NGAL (DY1757) and for TIM-1/KIM-1/HAVCR (DY1750) as adapted in the lab. In our hands the limit of detection for NGAL was 6-12 pg/ml while that of KIM-1 was 4-8 pg/ml depending on the day of assay. The slope of the dilutions of patient urine paralleled the dilution of the standard proteins. There was an intra-assay variation of 7.3% for NGAL and 6.9% for KIM-1 with inter-assay variations of 8.5% and 7.8% respectively. Using these assay systems, we measured urinary NGAL and KIM-1 levels in 8 normal control subjects, 21 patients with a histologic diagnosis of clear cell cancer, 8 with papillary cancer and 11 patients having surgery for non-kidney related issues. FIG. 1 shows Log urinary KIM-1 factored by tumor stage. Box-plot presentations with the median (black bar), mean (dot) and standard deviation (arrows). All results in Log (ng protein/mg creatinine). The results are expressed as the nanograms of urinary KIM-1 normalized per milligram of urinary creatinine and suggest there is no difference in the amount of urinary NGAL between normal subjects and patients that underwent partial or total nephrectomy for a renal tumor. In contrast, the urinary KIM-1 levels ranged from a mean and standard deviation of 0.035+/−0.027 ng/mg creatinine in normal subjects to 1.26+/−1.60 for all 21 patients with clear cell carcinoma, 0.79+/−0.43 for the 8 patients with papillary carcinoma and 0.03+/−0.04 ng/mg creatinine for the 11 control patients having surgery for non-kidney issues. Kruskal Wallis test on the amounts of urinary KIM-1 gave a p-value of 0.0001825 indicating a significant difference between levels in the normal subjects and all patient groups having renal tumors. The patients with clear cell carcinoma, papillary carcinoma and the control patients having surgery for non-kidney related issues were statistically indistinguishable as groups on the basis of age, gender mix, ethnicity, serum creatinine and the number of smokers (a risk factor for kidney cancer) as determined by statistical analysis by ANOVA, Fisher test, and Kruskal-Wallis tests. The estimated glomenilar filtration rates (eGFR) (MDRD equation) of these 3 patient groups was similarly indistinguishable since the age, gender, race and serum creatinine used to calculate this were each not significantly different. If the patients with a diagnosis of clear cell and papillary carcinoma are grouped by tumor staging, there is a statistically significant increase in the urinary KIM-1 with increase in stage (FIG. 1).

These results show that KIM-1 is differently expressed among stages 0, 1, 2 and 3 with a Kruskal Wallis test p-value of 1.97e-07 across all groups. Stage 2 was excluded from the calculation since only 2 patients had this diagnosis. The Wilcox test p-value comparing stage 0 (normal subjects and patients with non-renal surgery) to stage 1 is 7.85e-03 and to stage 3 is 4.07e-05. Taking the natural log transformation of tumor size and the urinary KIM-1 level for the 21 patients with a diagnosis of clear cell carcinoma gave a parametric Pearson correlation coefficient of 0.71 suggesting a reasonable association between these parameters. There was no such correlation with urinary NGAL levels and tumor stage. As a basis for comparison, the urinary NGAL level of 8 normal subjects was 0.60+/−0.34 ng/mg creatinine, 0.38+/−0.46 ng/mg creatinine for the 11 patients with non-kidney related surgery, 0.43+/−0.27 ng/mg creatinine for all 21 patients with a diagnosis of clear cell carcinoma, 0.76+/−0.33 ng/mg creatinine for the 8 patients with a diagnosis of papillary carcinoma but 54.2 ng/mg creatinine for a typical ICU patient with sepsis needing dialysis. Our preliminary studies suggest that while measurement of urinary KIM-1 levels differentiates patients with kidney cancer from normal subjects, essentially confirming previous studies (Vila, M. R., et al., Kidney international 65: 1761-1773, 2004; Han, W. K., et al., J. Am. Soc. Nephrol. 16: 1126-1134, 2005; Lin, F., et al., Am. J. Surg. Pathol. 31: 371-381, 2007), NGAL does not. A problem with KIM-1 is that it is a biomarker of kidney injury per se and if the kidney is still under repair from partial nephrectomy, a latent high urinary KIM-1 measurement may be reflective of this or a preexisting undetected chronic kidney disease rather than persistent tumor. Furthermore, while KIM-1 is a marker of kidney injury, it is a general marker like fever, in that it tells you something is wrong with the kidney but it does not tell you precisely what is wrong. This underscores the need for a biomarker or a series of biomarkers specific for kidney cancer rather than a marker of any kidney injury.

Example 2

Figure 2:
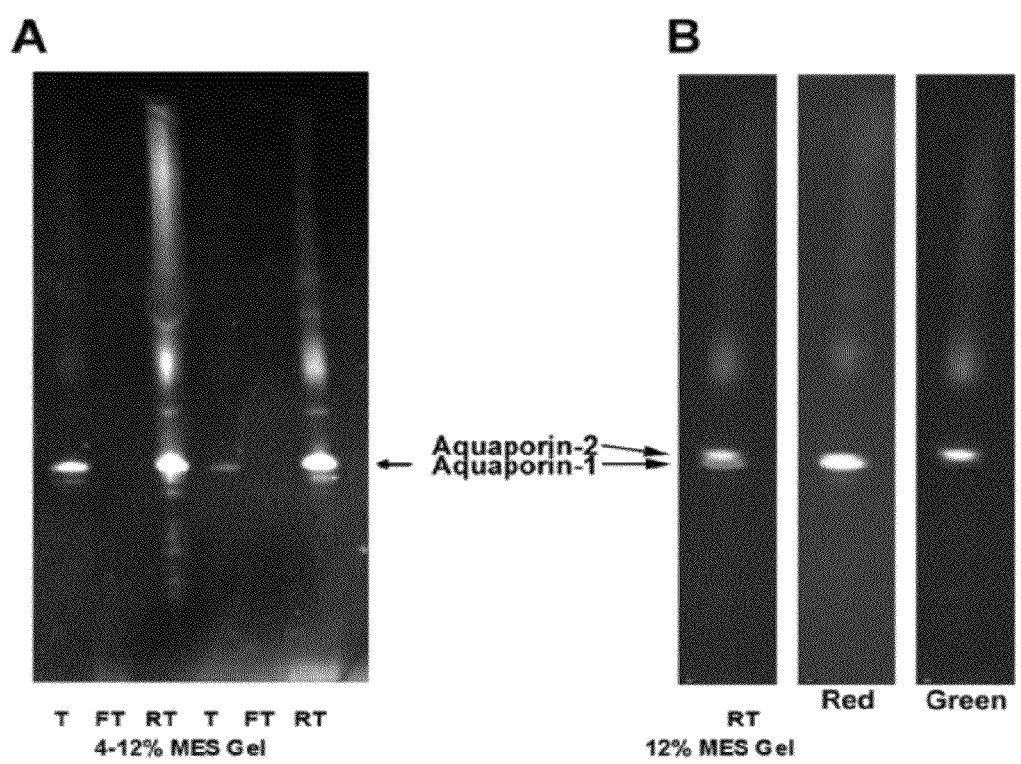
FIG. 2 illustrates Western blot for aquaporins 1 and 2 in urine and urinary exosome preparations. A: 4-12% MES Gel. B: 12% MES Gel. In B, left panel is a composite of green and red fluorescence; middle panel is red fluorescence (anti-AQP-1 antibody); right panel is green fluorescence (anti-AQP-2 antibody).

This example illustrates biomarker proteins of renal cell cancer. In these experiments, to measure AQP-1 and also to confirm its location in urinary exosomes, these structures were prepared from the urine of renal cancer patients by means of 100 kDa cut off Amicon centrifugal ultra-filters (Cheruvanky, A., et al., Am. J. Physiol. 292: F1657-F1661, 2007; Zhou, H., et al., Kidney Int'l. 69: 1471-1476, 2006) as adapted in our lab. Similar results (not shown) were obtained if the exosomes were prepared by high speed centrifugation. Acetone-methanol precipitated total urine protein, the flow-through from the ultra-filters and the filter retentates (exosomes and high molecular weight urinary proteins) were subject to Western blotting for AQP-1. FIG. 2 presents Western blots for aquaporins 1 and 2 in urine and urinary exosome preparations. Urinary proteins from two different patients were prepared. The total urine (T) prior to fractionation, flow through (FT) from the ultra-filter and filter retentates (RT) were separated on two different acrylamide gels. Rabbit polyclonal anti-aquaporin 1 (detected as red fluorescence) and goat polyclonal anti-aquaporin 2 (detected as green fluorescence) were used to visualize their respective proteins. The results show that AQP-1, a protein of about 29 kDa, is present in the 100 kDa retentates of urine and not in the flow through that represents soluble urine proteins with weights below 100 kDa. Aquaporin-2, a marker of collecting duct epithelia of the kidney (Takata, K., et al., Histochem Cell Biol 130: 197-209, 2008) is also found in urinary exosomes (Pisitkun, T, et al., Molecular & Cellular Proteomics 5: 1760-1771, 2006). Both water channels exist in the non-glycosylated form at about 29 kDa and glycosylated forms of higher weight which accounts for the streaking in the gels. The two proteins are not resolved by the 4-12% gradient gel (not shown) and are somewhat resolved on a 12% gel. These two proteins, however, may be visualized on the same gel by the judicious use of primary and secondary antibodies tagged with different florescent reporter molecules (FIG. 2, panel B).

Example 3

This example illustrates intra-operative (I) and post-operative (P) urinary AQP-1 and ADFP levels of patients with renal clear cell carcinoma.

Figure 3:
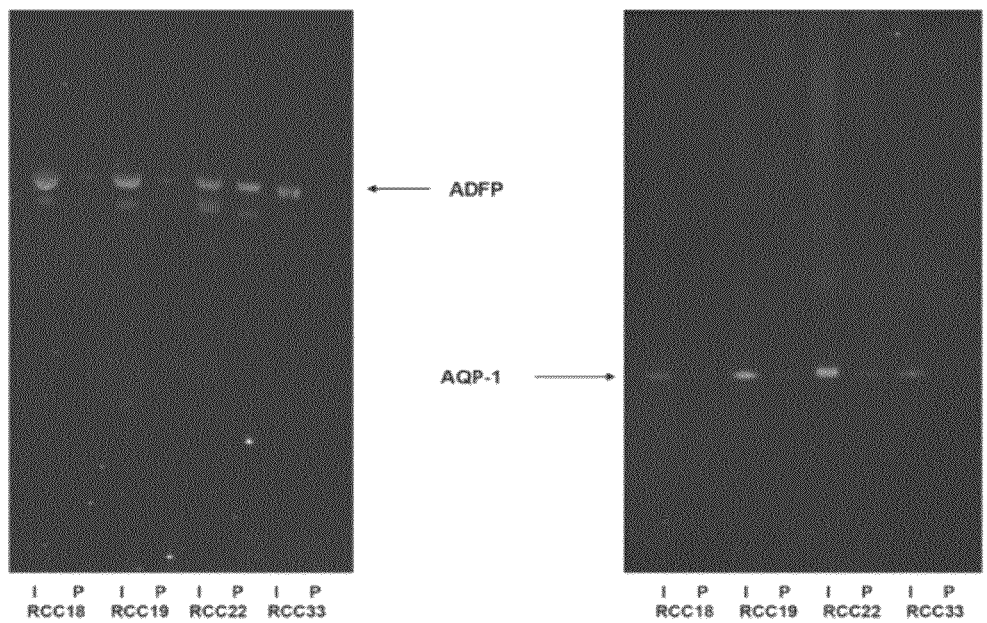
FIG. 3 illustrates intra-operative (I) and post-operative (P) urinary AQP-1 and ADFP levels of patients with renal clear cell carcinoma.
Figure 4:
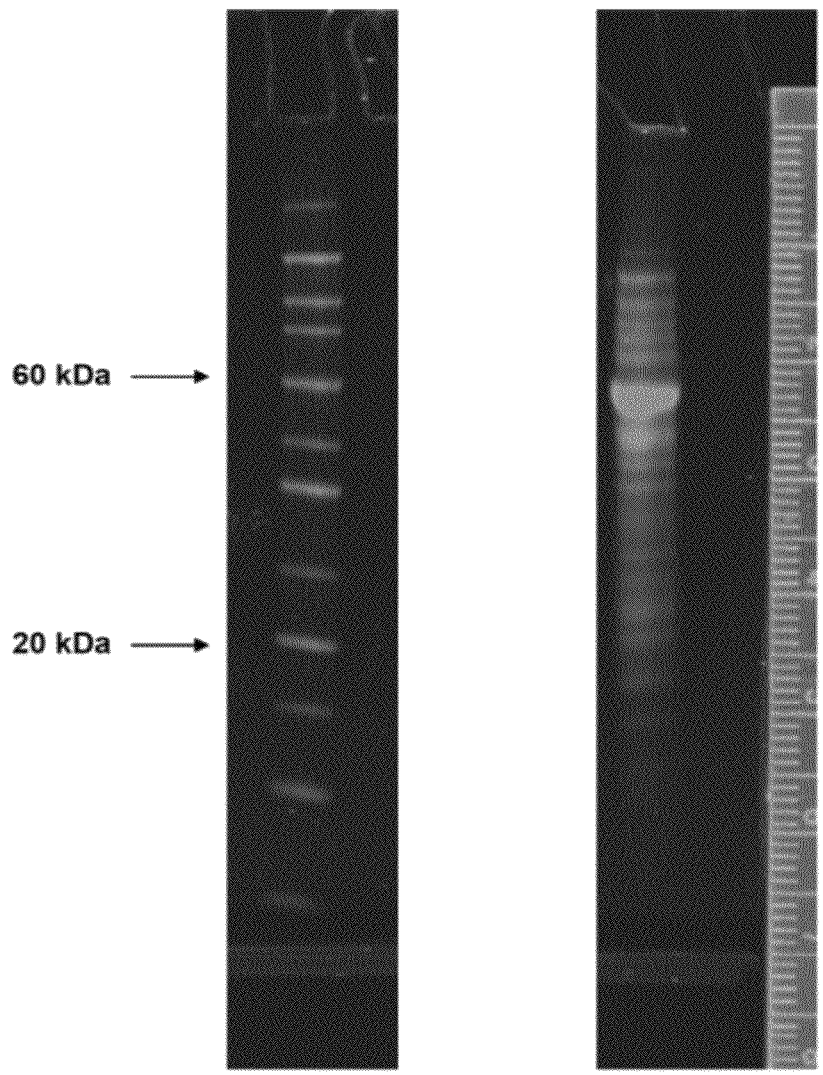
FIG. 4 illustrates a gel of urinary exosomal protein (right panel). Protein molecular weight standards in an adjacent lane are shown in left panel.

To test the concept of comparing biomarker levels in patient urine prior to surgery or intra-operatively to those levels one month following surgery, we measured AQP-1 and also ADFP in un-fractionated total urine. The four patients were diagnosed with clear cell carcinoma and the amount of total urine protein applied to the gel was normalized for the amount of creatinine excretion to correct for urine volume and any differential urine concentration. In these experiments, the protein load for each sample was adjusted for creatinine excretion. The results from 4 patients, shown in FIG. 3, represent total urine protein. These data indicate that the urinary excretion of AQP-1 in the intra-operative urine of the four patients is visibly elevated compared to that of their post-operative urines. In addition, the urinary AQP-1 and ADFP levels in the post-operative urines of these patients, after the tumor was removed, was significantly decreased compared to that of the intra-operative urine. On average there was a 70% decrease (p<0.02) decrease in ADFP and a 67% decrease (p<0.0001) in AQP-1 when digitized images were quantified. Upon tumor removal, both markers are significantly decreased in the urine. These data show that a biomarker found in urine can be used to identify and monitor a renal cancer. These data further show, along with the profile of exosome polypeptides illustrated in FIG. 4, that exosomes can be a source for markers suitable for patient diagnosis and prognosis without having to perform an invasive procedure for sample acquisition.

Example 4

This example illustrates using MS/MS spectra of an exosomal protein tryptic peptide separated by liquid chromatography to identify polypeptides.

Urinary exosomes are, in essence, a kind of tissue biopsy that appear in a non-invasive collection of urine but represent pieces of the cell of origin to and including cytosolic proteins (Zhou. H., et al., Kidney Int. 74: 613-621, 2008; Pisitkun, T, et al., Molecular & Cellular Proteomics 5: 1760-1771, 2006). Preparation of urinary exosomes by centrifugation in a way depletes the test sample of urinary albumin which could otherwise hide lower abundance proteins of potential interest. Exosomes can also be concentrated from urine by means of ultrafilter-retention but this also concentrates high molecular weight proteins.

Figure 5:
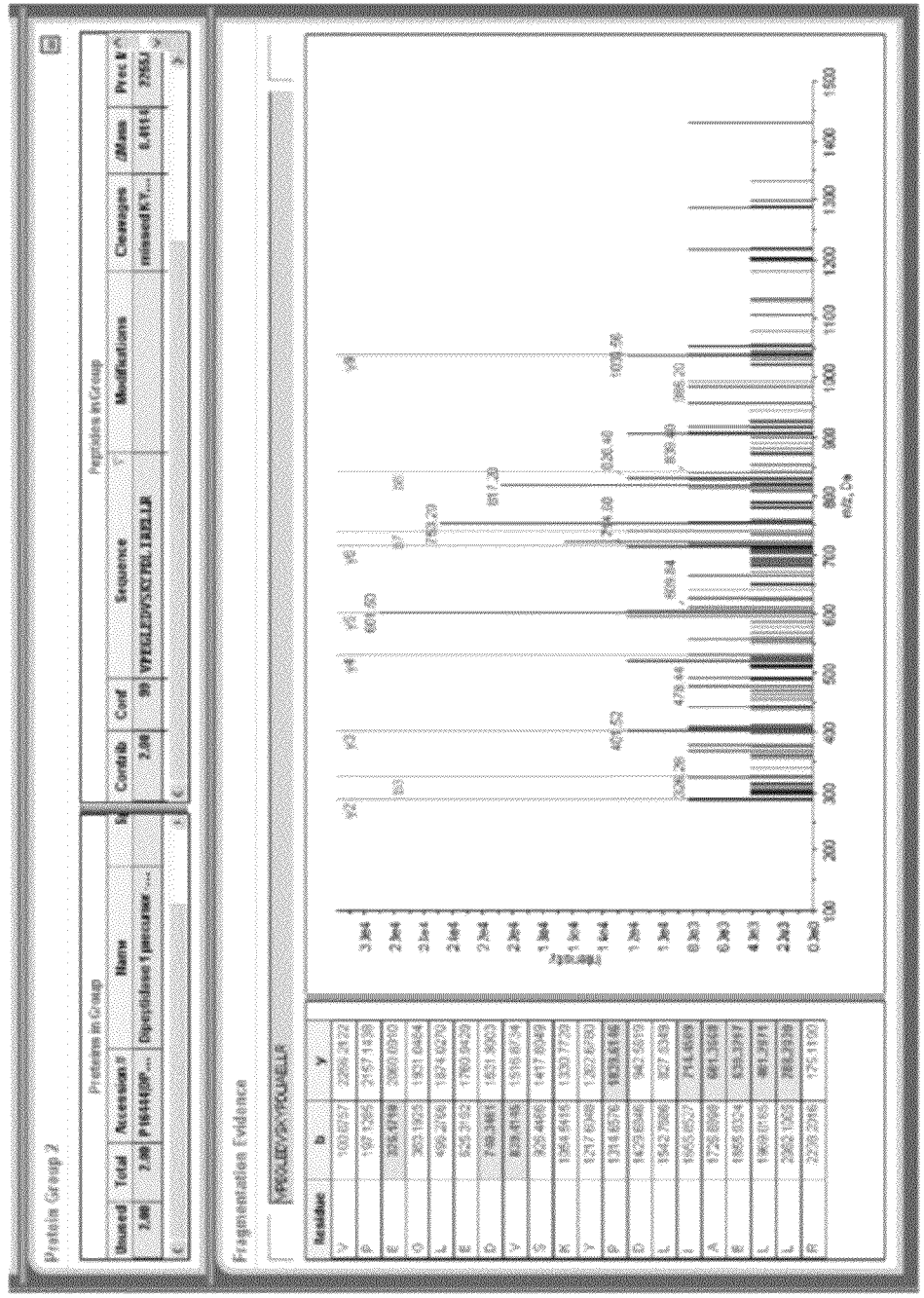
FIG. 5 illustrates MS/MS spectra of an exosomal protein tryptic peptide separated by liquid chromatography.

Exosome preparations and mass spectral analysis can be used to identify yet other biomarker proteins. Among the proteins found, the protein renal dipeptidase 1 was identified by Protein Pilot based upon an unsupervised top-down mass spectral analysis as shown in FIG. 5 and other peptide fragmentation patterns. The amount of this dipeptidase is substantially decreased in Wilm's tumor, a genetic contributor to renal cancer (Gokden, N., et al., Diagnostic Cytopathology 36: 473-477; 2008). ELISAs or other immune-based assays can be used to measure such proteins with sensitivities that cover their dynamic concentration range in whole urine.

Example 5

This example illustrates that AQP1 and ADFP concentrations in patients with either clear cell or papillary carcinoma can be significantly greater and distinguished from those in nonnephrectomy surgical control patients and the healthy individuals.

In these investigations, we analyzed 22 patients with clear cell carcinoma, 10 patients with papillary carcinoma, and the 15 controls undergoing surgery for non-kidney-related issues. These patients were statistically indistinguishable by age (3 groups: analysis of variance test P=0.51 (Table 1); clear cell cancer vs control: t test P=0.27; papillary cancer vs control: t test P=0.41) or by sex (Fisher exact test, 3 groups: P=0.30; clear cell cancer vs control: P=0.26; papillary cancer vs control: P=0.40). There were even age (t test P=0.98) and sex (Fisher exact test P>0.99) distributions between clear cell and papillary carcinoma groups. Comparatively, healthy volunteers were significantly younger. Differences in serum creatinine levels among the 3 groups were not significant (Kniskal-Wallis test P=0.07) (Table 1) and neither were differences between the 2 renal cancer subtypes vs controls (clear cell cancer vs control [P=0.09] and papillary cancer vs control: Wilcoxon rank sum test [P=0.06]). The eGFR was not different among the 3 groups (Kruskal-Wallis test P=0.07) (Table 1) or between the 2 renal cancer subtypes vs the control group (clear cell: Wilcoxon rank sum test P=0.09; papillary cancer: Wilcoxon rank sum test P=0.06). The frequency of smoking, a risk factor for kidney cancer, (Rini, B. I., et al., Lancet 373: 1119-1132, 2009; Parker, A., et al., Int. J. Urol. 15: 304-308, 2008) was not statistically different among the 3 groups (Fisher exact test P=0.08) or between those with clear cell cancer vs controls ($\chi^2$ test P=0.46) but differed between the papillary cancer and control groups ($\chi^2$ test P=0.04). The rate of smoking among the 3 groups was 57% for patients with clear cell cancer, 90% for those with papillary cancer, and 47% for surgical controls. Smoking history of the healthy volunteers was not assessed. Statistical analysis of sex, age, smoking, serum creatinine level, and eGFR was not performed for patients with oncocytoma (n=4), nonmalignant renal mass (n=5), and chromophobe renal cell carcinoma (n=1) because of the small number of individuals involved.

Figure 6:
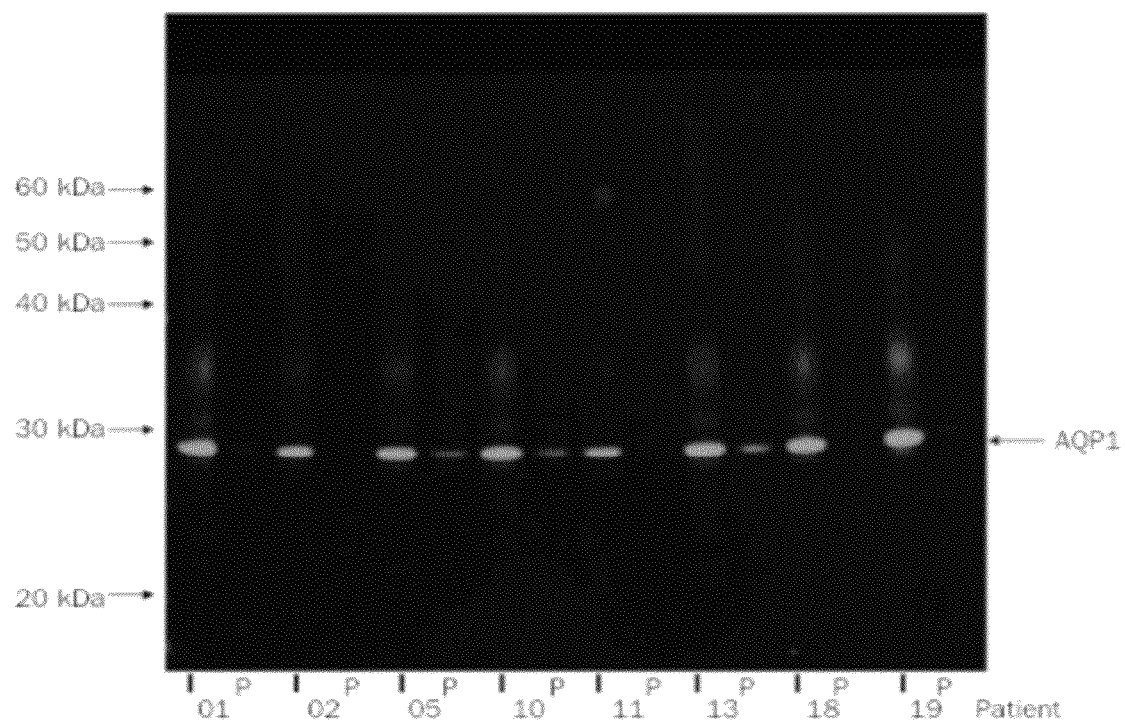
FIG. 6 illustrates a representative Western blot for AQP1 quantification.
Figure 7:
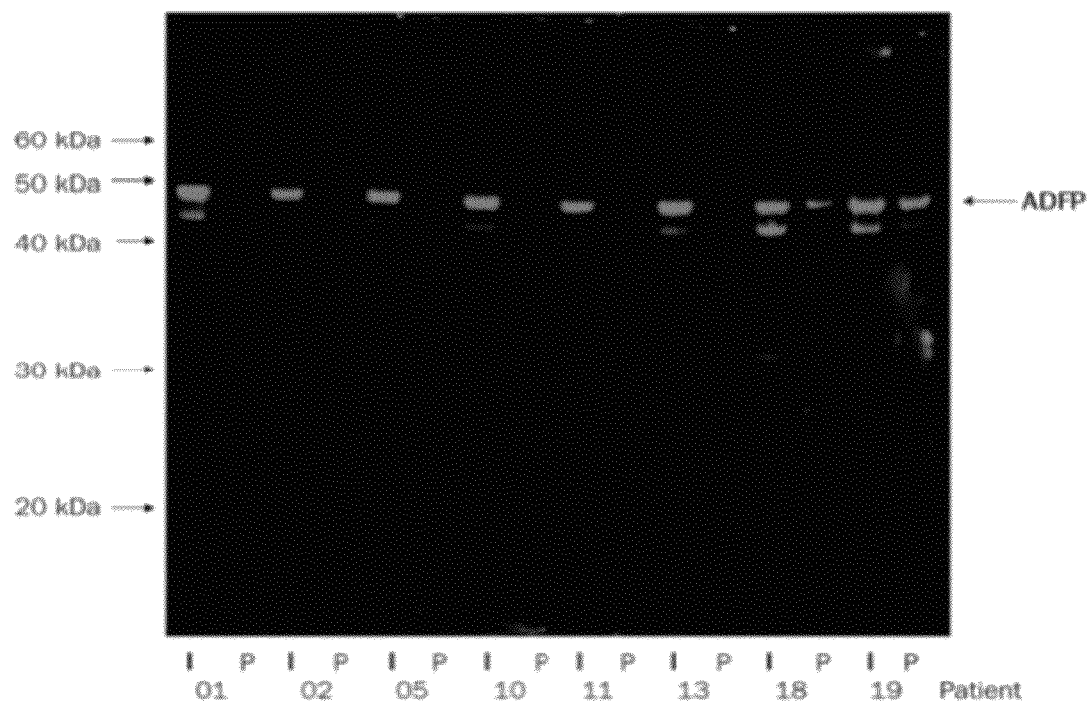
FIG. 7 illustrates a representative Western blot for ADFP quantification.
Figure 10:
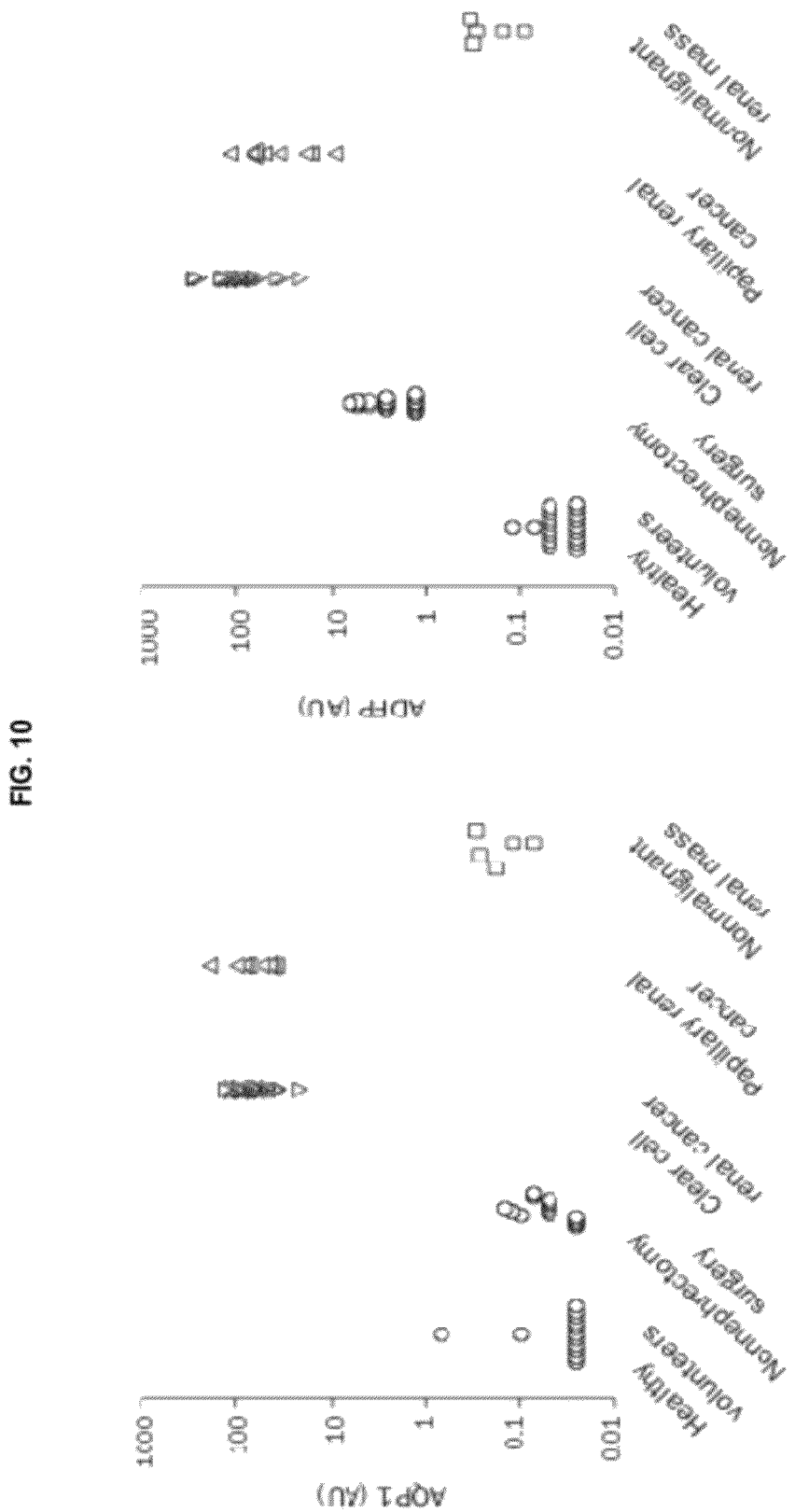
FIG. 10 illustrates urine aquaporin-1 (AQP1) (left) and adipophilin (ADFP) (right) concentrations in patients with and without renal cancer, and in healthy controls.

Urine concentrations of both AQP1 and ADFP in patients with renal cancer before tumor excision and in surgical and nonsurgical controls are shown individually in FIG. 10 and summarized in Table 2. Representative Western blots for AQP1 and ADFP quantification are shown in FIG. 6 and FIG. 7 respectively. The AQP1 and ADFP concentrations in patients with either clear cell or papillary carcinoma were significantly greater and clearly separated from those in the nonnephrectomy surgical control patients and the healthy individuals.

Figure 11:
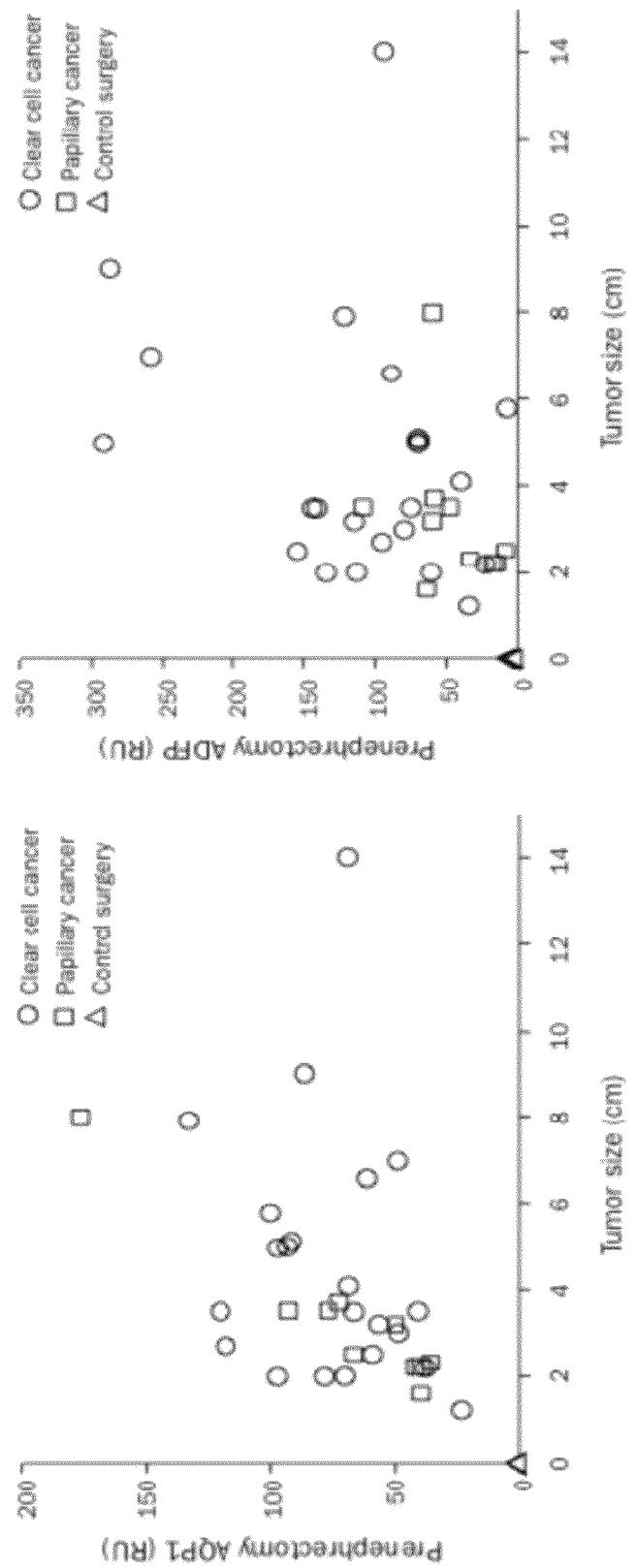
FIG. 11 illustrates relationship between tumor size and prenephrectomy urine aquaporin-1 (AQP1) (left) and adipophilin (ADFP) (right) concentrations, expressed in relative density units (RU), in patients with renal carcinoma (papillary cancer, n=22; clear cell cancer, n=10) and surgical controls.

FIG. 11 presents an analysis of the relationship between tumor size and prenephrectomy urine aquaporin-1 (AQP1) (left) and adipophilin (ADFP) (right) concentrations, expressed in relative density units (RU), in patients with renal carcinoma (papillary cancer, n=22; clear cell cancer, n=10) and surgical controls. Values are normalized for creatinine excretion. Analysis of the 32 patients with clear cell and papillary cancer and the surgical controls (n=15) bearing no tumor found a significant linear correlation between AQP1 concentration and tumor size (Spearman correlation coefficient=0.82; P<0.001; FIG. 11). A similar correlation was found for ADFP (r=0.76; P<0.0001; FIG. 11). If the Spearman analysis is confined to the 32 patients with clear cell and papillary kidney cancer, the correlation coefficient for AQP1 is 0.5 and remains significant at P=0.004 and 0.31 for ADFP, but this is not significant at P=0.08.

Example 6

This example illustrates that AQP1 concentrations in patients with oncocytoma can be statistically indistinguishable from those of the healthy controls.

In these investigations, four patients with oncocytoma, a benign growth of medullary origin, had preexcision urinary AQP1 concentrations that were statistically indistinguishable from those of the healthy controls and the surgical controls and significantly less than those of the patients with clear cell or papillary tumors. The 6 patients with a radiographically diagnosed renal mass having surgery for a presumptive diagnosis of renal carcinoma but subsequently diagnosed as having cystic nephroma (n=2), plasmacytoma, hemangioma, chromophobe kidney cancer (a malignant variety not of proximal origin), or angiomyolipoma had preexcision urinary AQP1 concentrations that were statistically indistinguishable from those of the healthy controls and the surgical controls and significantly less than those of patients with either clear cell or papillary carcinoma (Table 2). Furthermore, this pattern of low urinary biomarker excretion before the surgical removal of the tumor was also found to be true for ADFP concentrations in the patients with oncocytoma, non-malignant renal mass, and chromophobe carcinoma.

Example 7

This example illustrates the use of ROC curve analysis.

In these investigations, the sensitivity and specificity of urine AQP1 and ADFP for detecting renal cancer were determined using Receiver operating characteristic (ROC) curves. The results of AQP1 and ADFP tests in prenephrectomy urine samples of patients with clear cell or papillary renal cancer were considered true positive, and those in surgical controls were considered true negative.

Figure 8:
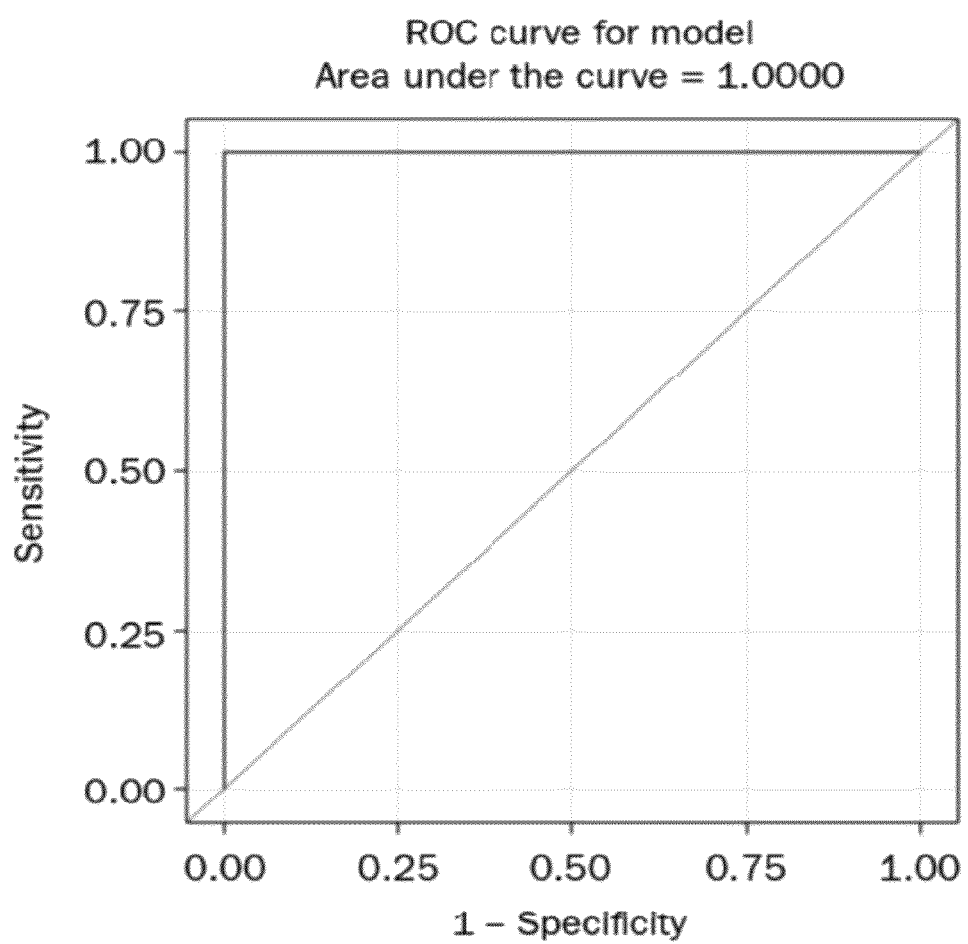
FIG. 8 illustrates a receiver operating characteristic (ROC) curve of the sensitivity and specificity of urinary aquaporin-1 (AQP1) to detect patients with clear cell or papillary kidney cancer.
Figure 9:
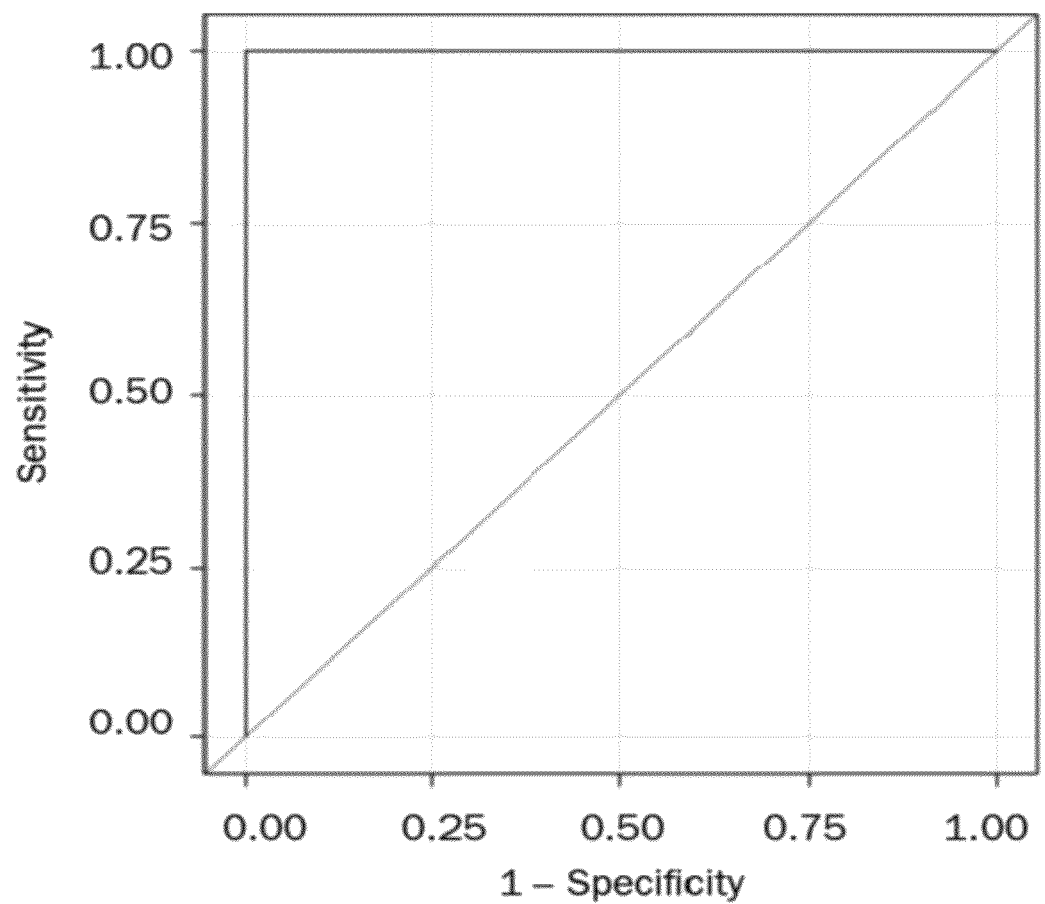
FIG. 9 illustrates a receiver operating characteristic (ROC) curve of the sensitivity and specificity of urinary adipofiling (ADFP) to detect patients with clear cell or papillary kidney cancer.

FIG. 10 presents Urine aquaporin-1 (AQP1) (left) and adipophilin (ADFP) (right) concentrations in patients with and without renal cancer and in healthy controls. Concentrations were determined by Western blot analysis, expressed in arbitrary density units (AU), and normalized to urine creatinine concentration. Each data point is a single individual. Results are shown on a log scale. Because there is clear separation in relative amounts of both AQP1 and ADFP between the surgical control patients and the cancer patients (FIG. 10), area under the ROC curve for each marker is 1.00 (FIG. 8 and FIG. 9). Therefore, for both AQP1 and ADFP, there was 100% sensitivity and 100% specificity in detecting renal cancer, achievable along a variety of threshold values. It follows that ROC curve analysis between patients with renal cancer and healthy controls is the same as for the surgical controls (data not shown).

Figure 12:
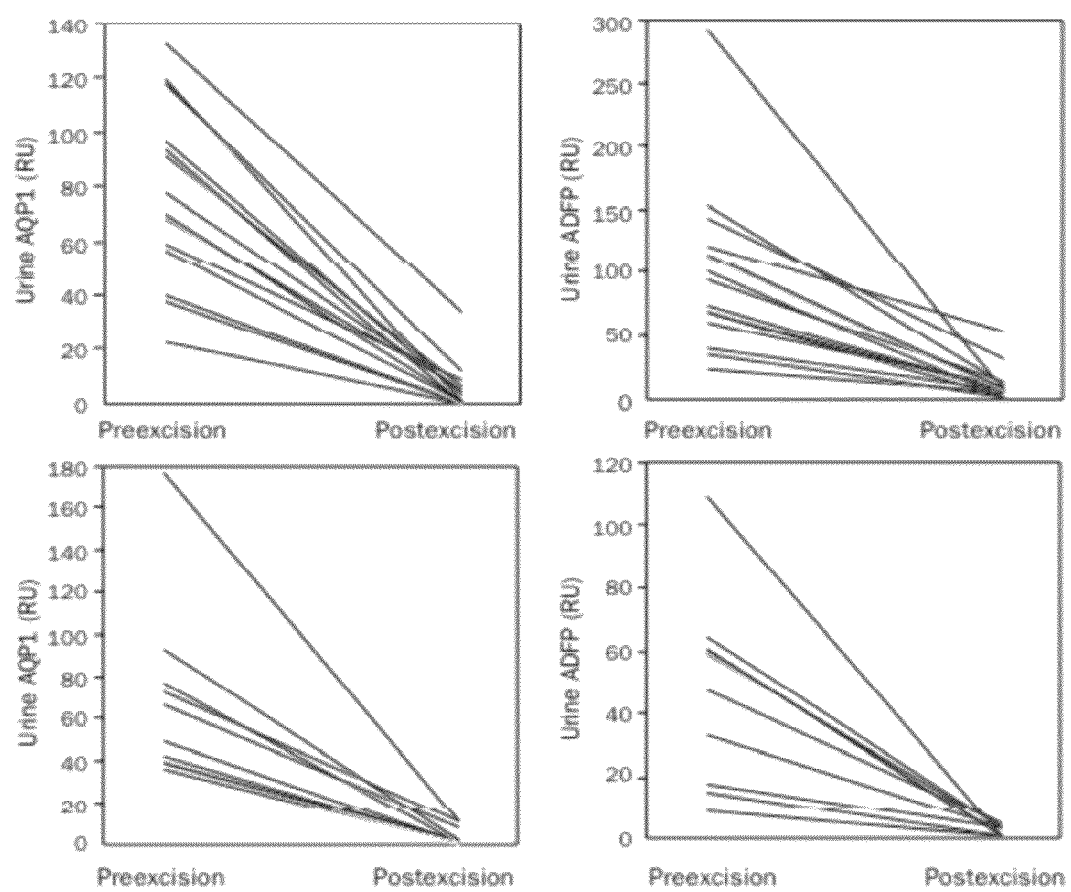
FIG. 12 illustrates change in urinary aquaporin-1 (AQP1) (left) or adipophilin (ADFP) (right) concentrations, expressed in relative density units (RU), after partial or total uninephrectomy in patients with clear cell renal carcinoma (n=15, top) or papillary carcinoma (n=10, bottom).

FIG. 12 illustrates Change in urinary aquaporin-1 (AQP1) (left) or adipophilin (ADFP) (right) concentrations, expressed in relative density units (RU), after partial or total uninephrectomy in patients with clear cell renal carcinoma (n=15, top) or papillary carcinoma (n=10, bottom). Values are normalized for creatinine excretion. Of the 33 patients in the study with a diagnosis of renal carcinoma, 15 with clear cell and all 10 patients with papillary carcinoma returned for a surgical follow-up visit (average of 27 days) postoperatively and provided a urine sample, as did all the 15 surgical controls (average of 32 days). Urinary AQP1 and ADFP concentrations in the postoperative urine samples of the patients with renal cancer, after tumor removal, were significantly decreased compared with those of the preexcision urine samples (FIG. 12 and Table 2). There was a 95% decrease in urinary AQP1 concentration and an 88% decrease in ADFP concentration in the 15 patients with clear cell carcinoma. After tumor excision, there was a 97% decrease in AQP1 concentration and a 92% decrease in ADFP concentration in the 10 patients with papillary renal carcinoma.

All publications, patent applications, patents, and other references cited herein are incorporated by reference, each in its entirety.

TABLE 1

Characteristics of Healthy Volulnteers, Surgical Controls, and Patients With Various Types of Renal Cancer[a]

| | Healthy volunteers (n = 19) | Surgical controls (n = 15) | Clear cell renal cancer patients (n = 22) | Papillary renal cancer patients (n = 10) | Oncocytoma patients (n = 4) | Nonmalignant renal mass patients (n = 5) | Chromophobe cancer patient (n = 1) | P value |
|---|---|---|---|---|---|---|---|---|
| Sex, M/F, No. | 12/7 | 9/6 | 18/4 | 8/2 | 4/0 | 3/2 | 0/1 | .30[c] |
| Smoker, Y/N, No. | ND | 7/8 | 13/9 | 9/1 | 1/3 | 3/2 | 0/1 | .08[c] |
| Age (y), mean ± SD | 46 ± 12 | 62 ± 12 | 58 ± 12 | 58 ± 14 | 67 ± 4 | 59 ± 18 | 55 | .51[d] |
| Serum creatinine (mg/dL)[b] mean ± SD | ND | 0.9 ± 0.4 | 1.0 ± 0.3 | 1.2 ± 0.5 | 1.1 ± 0.2 | 1.7 ± 0.9 | 0.8 | .07e |
| eGFR (mL/min per 1.73 m$^2$)[b] mean ± SD | ND | 105 ± 38 | 87 ± 35 | 78 ± 33 | 76 ± 13 | 55 ± 35 | 80 | .07[e] |

[a]eGFR = estimated glomerular filtration rate; ND = not done.
[b]SI conversion factors: To convert serum creatinine values to µmol/L, multiply by 88.4; to convert eGFR values to mL/s per m2, multiply by 0.0167.
[c]Fisher exact test: surgical controls vs clear cell cancer vs papillary cancer.
[d]Analysis of variance: surgical controls vs clear cell cancer vs papillary cancer.
[e]Kruskal-Wallis test: surgical controls vs clear cell cancer vs papillary cancer.

TABLE 2

Mean ± SD Urinary AQP1 and ADFP Concentrations in Healthy Volunteers, Surgical Controls, and Patients With Various Types of Renal Cancer

|  | Urine AQP1 concentration (AU) | | Urine ADFP concentration (AU) | |
| --- | --- | --- | --- | --- |
|  | Preexcision (intraoperative) | Postexcision (postoperative) | Preexcision (intraoperative) | Postexcision (postoperative) |
| Healthy volunteers (n = 19) | 0.05 ± 0.15 |  | 0.04 ± 0.02 |  |
| Surgical controls (n = 15) | 0.06 ± 0.04 | 0.04 ± 0.06 | 2.8 ± 1.7 | 2.6 ± 1.4 |
| Clear cell renal cancer patients (n = 22) | 76 ± 29 | 5.0 ± 0.9 | 117 ± 74 | 11 ± 14 |
| Papillary renal cancer patients (n = 10) | 69 ± 42 | 3.3 ± 4.6 | 48 ± 30 | 2.7 ± 1.6 |
| Oncocytoma patients (n = 4) | 0.10 ± 0.11 | 0.10 ± 0.18 | 0.12 ± 0.15 | 0.14 ± 0.23 |
| Nonmalignant renal mass patients (n = 5) | 0.18 ± 0.09 | 0.17 ± 0.10 | 0.24 ± 0.11 | 0.21 ± 0.13 |
| Chromophobe cancer patient (n = 1) | 0.19 | 0.19 | 0.24 | 0.24 |
| P values: | | | | |
| Kruskal-Wallis test for healthy volunteers vs surgical controls vs oncocytoma group vs nonmalignant renal mass group vs clear cell group vs papillary group | <.001 |  | <.001 |  |
| Wilcoxon rank sum test for healthy volunteers vs nonmalignant renal mass group | .003 |  | .001 |  |
| Wilcoxon rank sum test for healthy volunteers vs oncocytoma group | .09 |  | .17 |  |
| Wilcoxon rank sum test for surgical controls vs healthy volunteers | .001 |  | .002 |  |
| Wilcoxon rank sum test for surgical controls vs oncocytoma group | .88 |  | .008 |  |
| Wilcoxon signed rank test within clear cell group before vs after excision |  | <.001 |  | <.001 |
| Wilcoxon signed rank test within papillary group before vs after excision |  | .002 |  | .002 |

Biomarker concentrations are normalized to urine creatinine concentrations.
ADFP = adipophilin;
AQP1 = aquaporin-1;
AU = arbitrary density units.

What is claimed is:

1. A method of detecting a renal cancer selected from the group consisting of a clear cell carcinoma, a papillary carcinoma and a combination thereof in a subject, the method comprising:

providing a urine sample from a subject suspected of having a renal cancer selected from the group consisting of a clear cell carcinoma, a papillary carcinoma and a combination thereof;

contacting the urine sample with at least one antibody that binds aquaporin-1 (AQP1), under conditions sufficient for formation of a primary complex comprising the at least one antibody and the AQP1 if present;

measuring quantity of the primary complex;

comparing the quantity of the primary complex to that of a control complex formed from the at least one antibody and a urine sample of an individual who does not have a renal cancer selected from the group consisting of a clear cell carcinoma, a papillary carcinoma and a combination thereof; and detecting a renal cancer selected from the group consisting of a clear cell carcinoma, a papillary carcinoma and a combination thereof in the subject if the primary complex comprises the AQP1 at a statistically significant elevated level compared to the control complex.

2. A method of detecting a renal cancer selected from the group consisting of a clear cell carcinoma, a papillary carcinoma and a combination thereof in accordance with claim 1, wherein the at least one antibody is a monoclonal antibody.

3. A method of detecting a renal cancer selected from the group consisting of a clear cell carcinoma, a papillary carcinoma and a combination thereof in accordance with claim 1, wherein the detecting comprises an immunoprecipitation assay, an ELISA, a radioimmunoassay, a Western blot assay, a dip stick assay, or a bead assay.

4. A method of detecting a renal cancer selected from the group consisting of a clear cell carcinoma, a papillary carcinoma and a combination thereof in accordance with claim 1, wherein the contacting comprises:
 a) contacting the urine sample with a solid surface that binds the AQP-1 if present; and
 b) subsequent to a), contacting the surface with the at least one antibody.

5. A method of detecting a renal cancer selected from the group consisting of a clear cell carcinoma, a papillary carcinoma and a combination thereof in accordance with claim 1, wherein the at least one antibody is bound to a polystyrene bead.

6. A method of detecting a renal cancer selected from the group consisting of a clear cell carcinoma, a papillary carcinoma and a combination thereof in accordance with claim 1, further comprising:
 contacting a control urine sample from a person not suspected of having a renal cancer selected from the group consisting of a clear cell carcinoma, a papillary carcinoma and a combination thereof with the at least one antibody that binds AQP-1 under conditions sufficient for formation of a control complex comprising the at least one antibody and the AQP-1 if present; and
 measuring quantity of the control complex.

\* \* \* \* \*